United States Patent
Pflum

(10) Patent No.: US 10,429,397 B2
(45) Date of Patent: Oct. 1, 2019

(54) CELL PERMEABLE ATP ANALOG FOR KINASE-CATALYZED BIOTINYLATION

(71) Applicant: WAYNE STATE UNIVERSITY, Detroit, MI (US)

(72) Inventor: Mary Kay Pflum, Northville, MI (US)

(73) Assignee: WAYNE STATE UNIVERSITY, Detroit, MI (US)

(*) Notice: Subject to any disclaimer, the term of this patent is extended or adjusted under 35 U.S.C. 154(b) by 0 days.

(21) Appl. No.: 15/187,206

(22) Filed: Jun. 20, 2016

(65) Prior Publication Data
US 2016/0377626 A1 Dec. 29, 2016

Related U.S. Application Data

(60) Provisional application No. 62/181,557, filed on Jun. 18, 2015.

(51) Int. Cl.
C07H 19/20 (2006.01)
A61K 31/70 (2006.01)
(Continued)

(52) U.S. Cl.
CPC .......... G01N 33/82 (2013.01); C07H 19/20 (2013.01); C08B 37/003 (2013.01); C08L 5/08 (2013.01); G01N 33/581 (2013.01); A61K 9/14 (2013.01)

(58) Field of Classification Search
CPC .................... C07H 19/20; A61K 9/14
(Continued)

(56) References Cited

PUBLICATIONS

Green et al. "Kinase-catalyzed biotinylation for phosphoprotein detection," JACS 2007 vol. 129, pp. 10-11.*
(Continued)

*Primary Examiner* — Shengjun Wang
(74) *Attorney, Agent, or Firm* — Brooks Kushman P.C.

(57) ABSTRACT

A cell permeable ATP analog has the following formula:

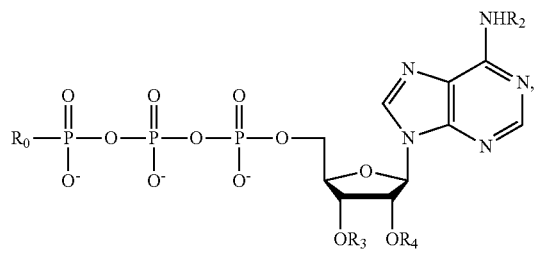

or a physiologically acceptable salt thereof,
wherein:
$R_0$ is (Continued)

-continued

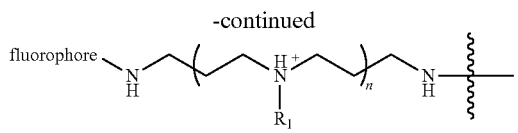

n, o, p are each independently 1, 2, 3, 4, 5, or 6, m is 0, 1, 2, 3, 4, or 5; X is O, S, NH, or $CH_2$. $R_1$ is H or $C_{1-6}$ alkyl, $R_2$ is H, $C_{1-6}$ alkyl, $C_{6-30}$ aryl, $C_{5-32}$ heteroaryl, or $C_{7-32}$ alkylaryl; $R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

23 Claims, 32 Drawing Sheets

(51) Int. Cl.
*A61K 9/14* (2006.01)
*G01N 33/82* (2006.01)
*C08B 37/08* (2006.01)
*G01N 33/58* (2006.01)
*C08L 5/08* (2006.01)

(58) Field of Classification Search
USPC .................................. 536/26.12; 424/489
See application file for complete search history.

(56) References Cited

PUBLICATIONS

Suwal et al. "Structural analysis of nATP analogues compatible with kinase catalyzed labeling," Bioconjugate Chemistry, 2012, vol. 23, pp. 2386-2391.*
Albarella, J.P. et al., "Monoadduct forming photochemical reagent for labeling nucleic acids for hybridization," Nucleic Acids Research, v. 17, n. 11, 1989, pp. 4293-4308.
Fouda, A.E. et al., "A cell permeable ATP analog for kinase-catalyzed biotinylation," Angew Chem Int Ed Engl., 54 (33), 2015, pp. 9618-9621.
Garcia, J. et al., "Total synthesis of the natural isoprenylcysteine carboxyl methyltransferase inhibitor spermatinamine," Tetrahedron Letters 50 (2009), pp. 5028-5030.

\* cited by examiner

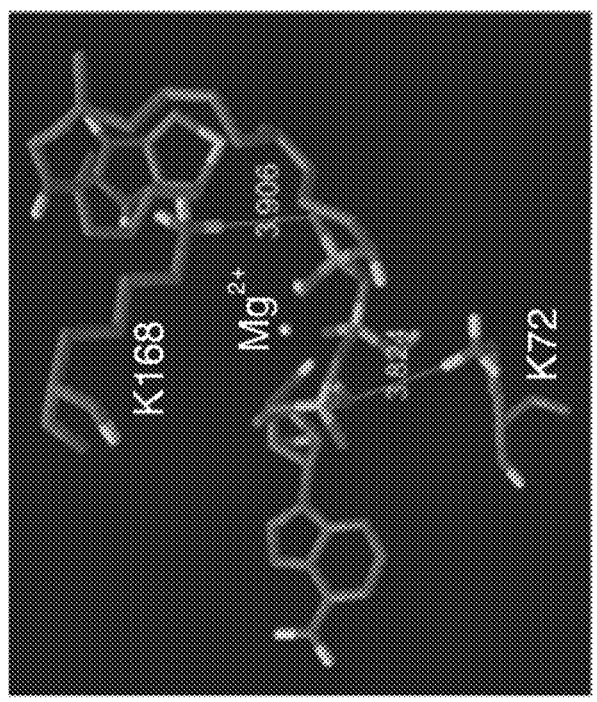
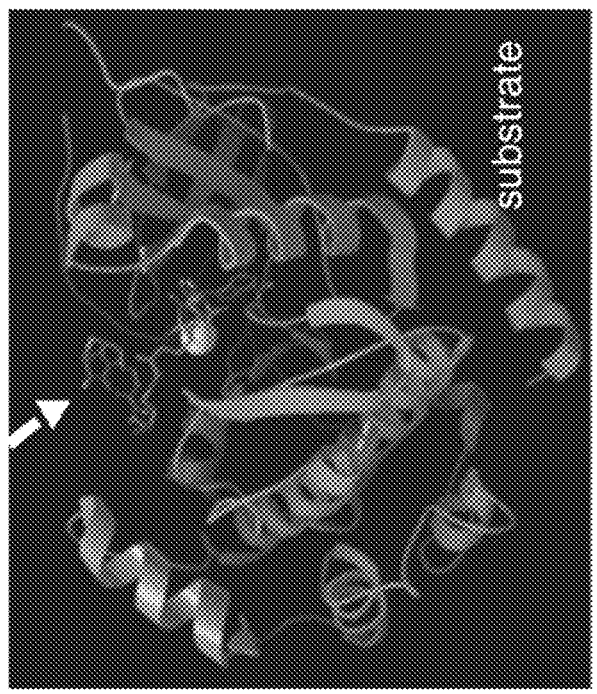
Fig. 2A
Fig. 2B

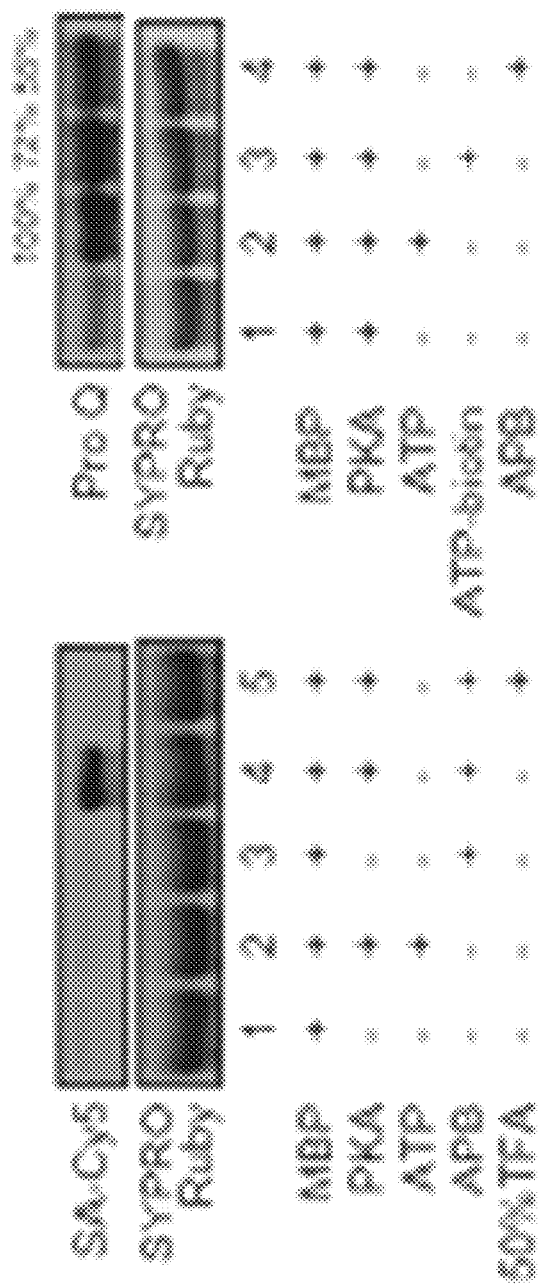

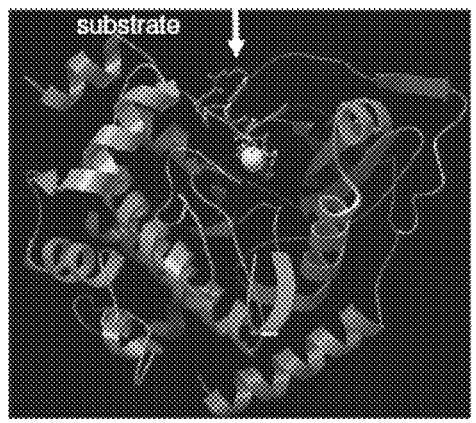 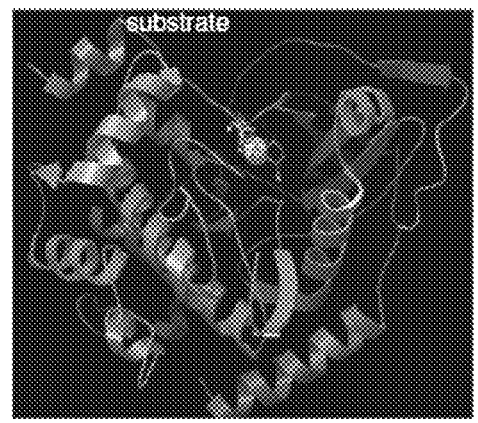
*Fig. 5A*  *Fig. 5B*
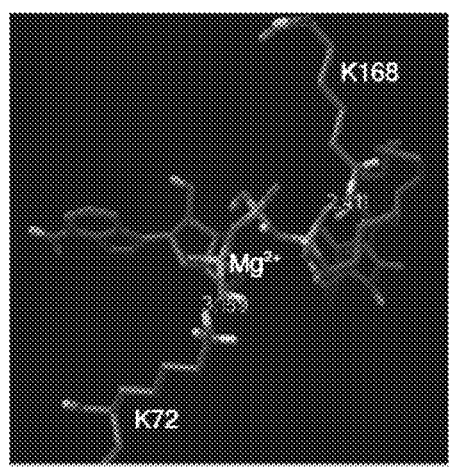 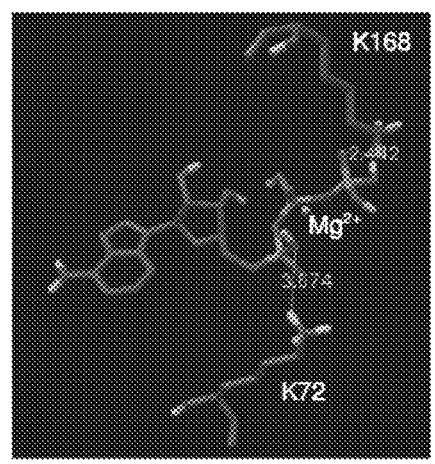
*Fig. 5C*  *Fig. 5D*

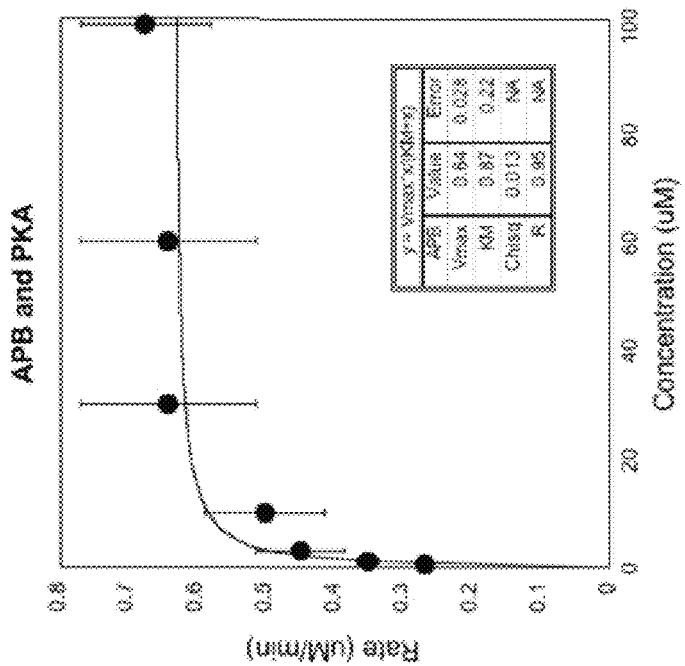
*Fig. 17B*
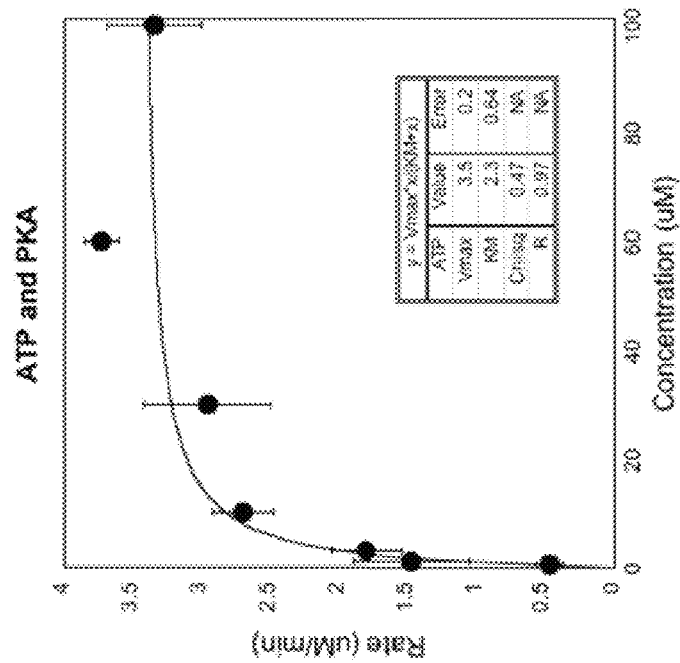
*Fig. 17A*
| | ATP | APB |
|---|---|---|
| $K_M$ (µM) | 2.3 ± 0.6 | 0.87 ± 0.21 |
| $V_{max}$ (µM/min) | 3.5 ± 0.2 | 0.64 ± 0.02 |
| $k_{cat}$ (s$^{-1}$) | 1.2 ± 0.1 | 0.22 ± 0.01 |
| $k_{cat}/K_M$ (µM s)$^{-1}$ | 0.52 | 0.25 |
*Fig. 17C*

| Concentration (mM) | % cell viability |
|---|---|
| 0.0 | 100% |
| 1.0 | 99 ± 3 % |
| 5.0 | 96 ± 1 % |
| 10 | 80 ± 4 % |
| 15 | 60 ± 6 % |
| 20 | 43 ± 3 % |
| 30 | 34 ± 2 % |

ATP, X= O
ATP-biotin, X=

APB, X=

Deacetylated Chitosan (DC), 3

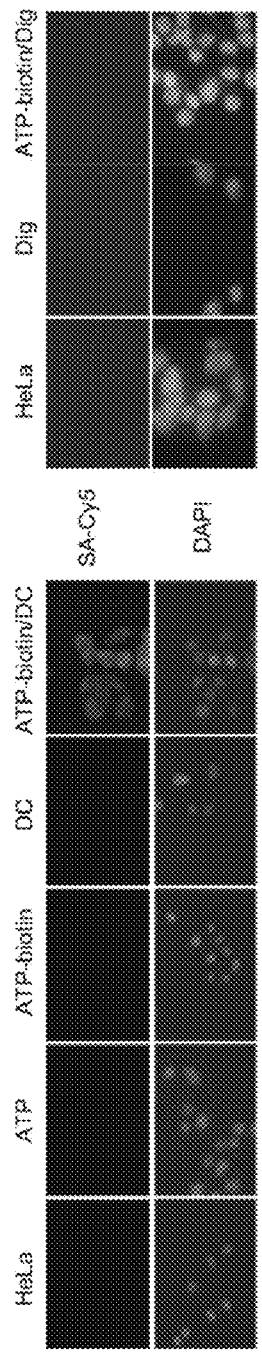
*Fig. 22A*
*Fig. 22B*
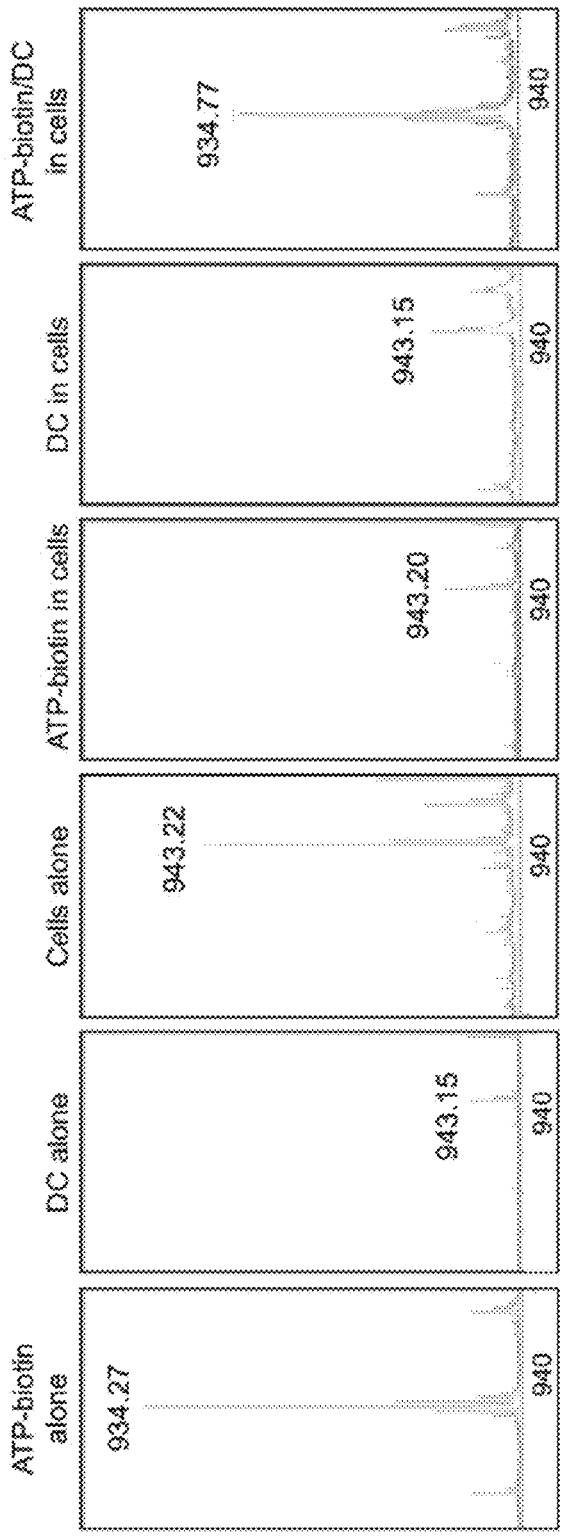
*Fig. 22C*

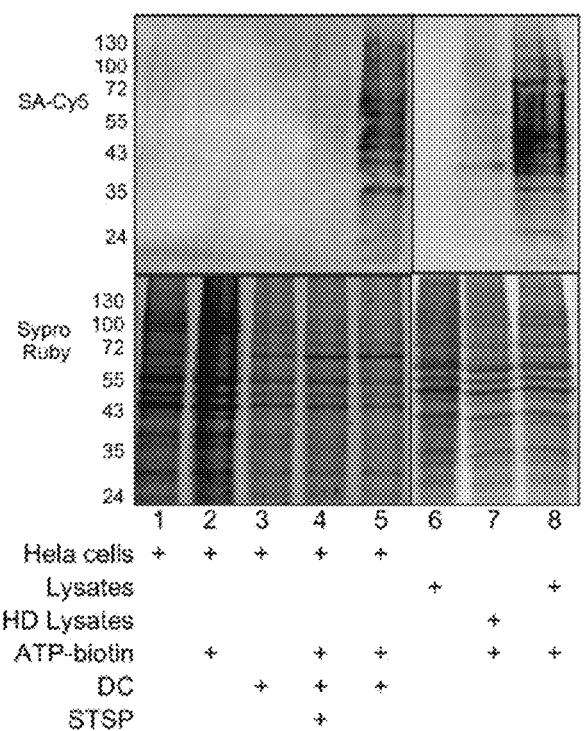
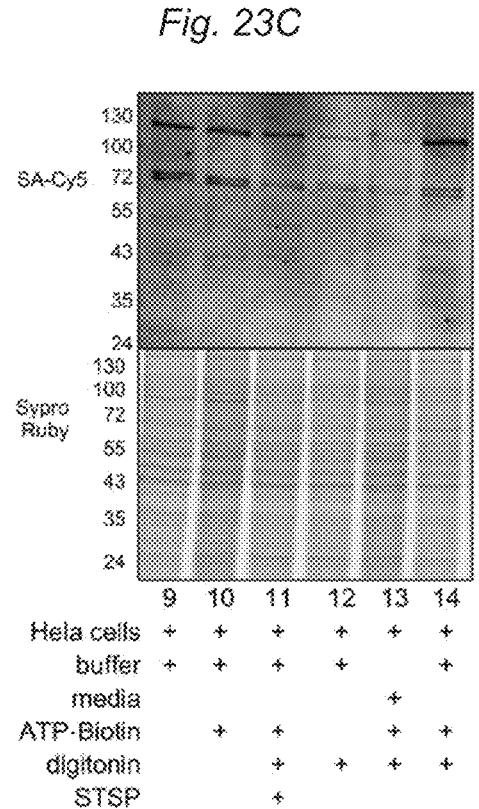
Fig. 23A  Fig. 23B  Fig. 23C

| ATP-biotin (mM) | DC (mg/mL) | % viable cells |
|---|---|---|
| 1 | 0.9 | 95 ± 7 % |
| 2 | 1.88 | 85 ± 8 % |
| 4 | 3.75 | 79 ± 5 % |
| 8 | 7.5 | 52 ± 4 % |
| 10 | 9.4 | 37 ± 1 % |

Fig. 24B

| ATP-biotin/DC in: | % viable cells |
|---|---|
| buffer | 55 ± 3 % |
| media | 67 ± 4 % |

Fig. 24C

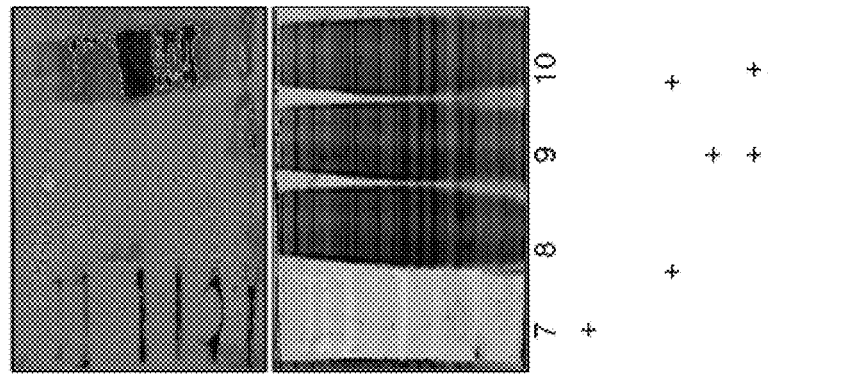
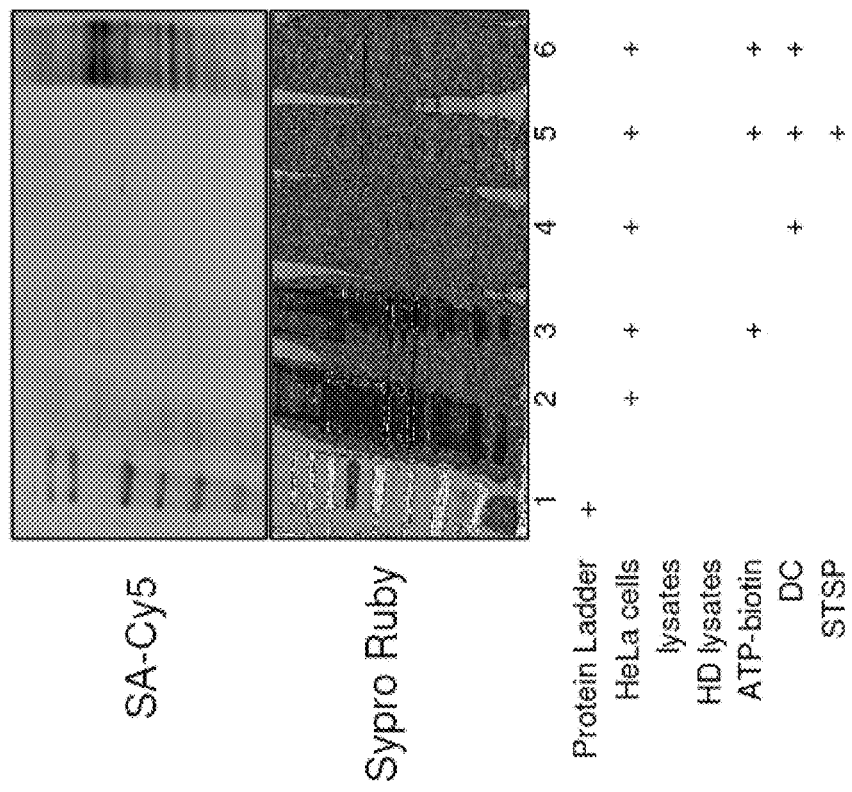
*Fig. 28C*
*Fig. 28D*

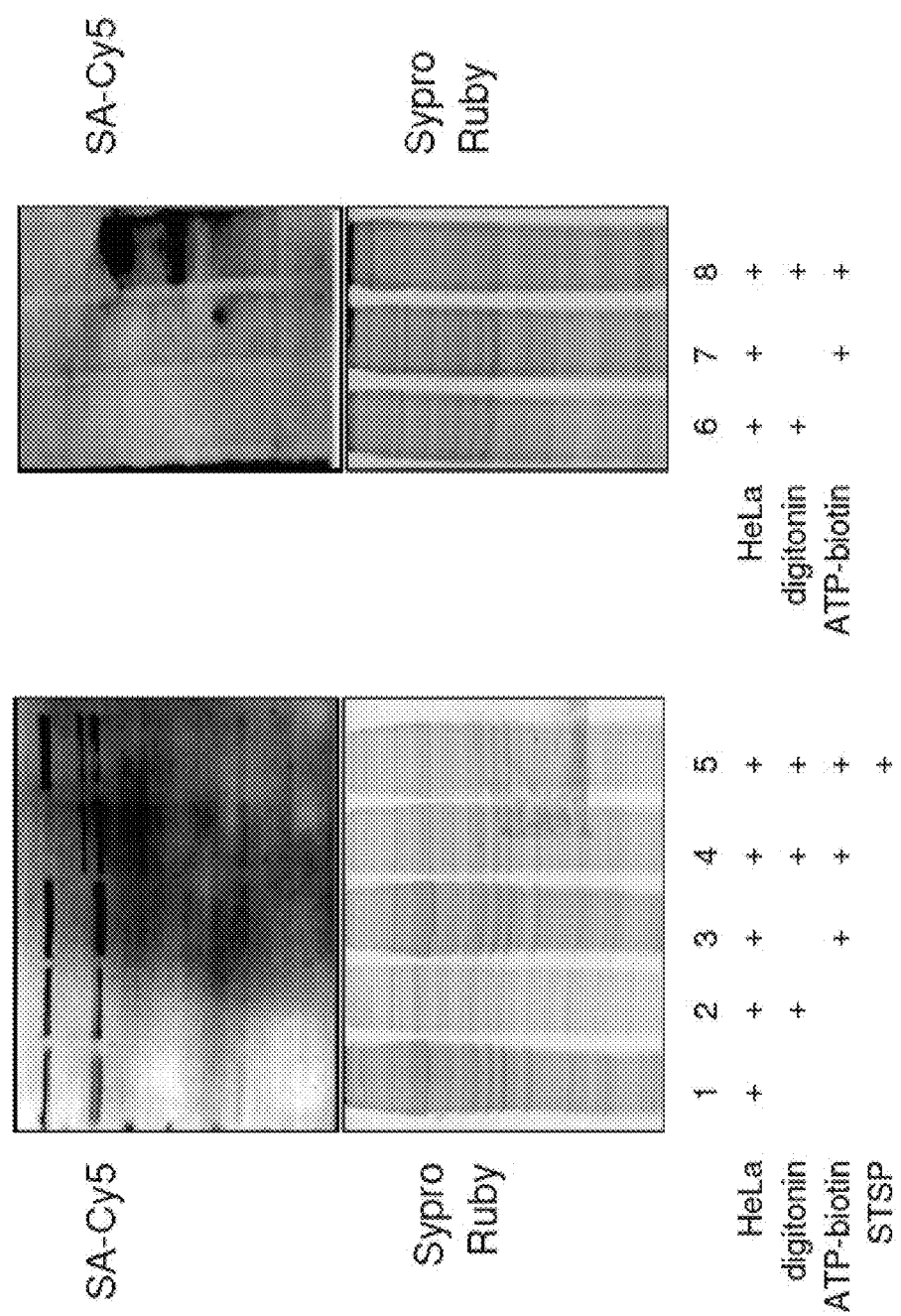

CELL PERMEABLE ATP ANALOG FOR KINASE-CATALYZED BIOTINYLATION

CROSS-REFERENCE TO RELATED APPLICATIONS

This application claims the benefit of U.S. provisional application Ser. No. 62/181,557 filed Jun. 18, 2015, the disclosure of which is hereby incorporated in its entirety by reference herein.

STATEMENT REGARDING FEDERALLY SPONSORED RESEARCH OR DEVELOPEMENT

This invention was made government support under GM079729 awarded by the National Institutes of Health. The government has certain rights in the invention.

TECHNICAL FIELD

In at least one aspect, the present invention relates to cell permeable ATP analogs.

BACKGROUND

Living cells respond to extracellular conditions through signaling cascades, which are mediated by a variety of protein modification reactions. One ubiquitous protein modification that regulates many metabolic and cell signaling pathways is kinase-catalyzed protein phosphorylation (FIG. 1A). Alteration of pathways involving kinases and phosphorylation can lead to diseases, such as Parkinson's, cancer and diabetes mellitus. Therefore, studying protein kinases and their phosphorylated substrates is critical to understand cell signaling pathways in both diseased and healthy cells.

With over 500 kinases and potentially thousands of phosphoproteins, multiple complementary approaches are necessary to monitor the complex cellular phosphoproteome. One powerful approach exploits analogs of the universal co-substrate of kinases, adenosine-5'-triphosphate (ATP, FIG. 1B). Multiple ATP analogs have been employed in kinase research, including base modified, sugar modified, and triphosphate modified analogs. Certain γ-phosphate modified ATP analogs have been used to label kinase substrates for subsequent purification and analysis. For example, ATP-biotin (1, FIG. 1B) is promiscuously accepted as a cosubstrate by protein kinases to phosphorylbiotinylate substrates. After kinase-catalyzed biotinylation with ATP-biotin, the biotin group facilitates analysis of phosphoproteins using various commercial streptavidin-conjugated reagents. Unfortunately, due to the impermeability of ATP analogs, ATP-biotin has been used in vitro only. The ability to utilize ATP-biotin in living cells would promote the study of protein kinases in more physiologically relevant conditions.

Accordingly, there is a need for cell-permeable ATP-biotin analogues.

SUMMARY

The present invention solves one or more problems of the prior art by providing a cell permeable ATP-biotin analog for live cell kinase-catalyzed biotinylation. Characteristically, the PEG linker of ATP-biotin is replaced with a polyamine linker to create ATP-polyamine-biotin 2 (APB, FIG. 1). In the case of APB, the polyamine linker will be positively charged under physiological conditions to partially neutralize the triphosphate charge and promote cell permeability. Spermine is chosen as the linker because its size mimics the original poly ethylene glycol (PEG) linker in ATP-biotin (FIG. 1). In addition, methylated spermine is used to avoid possible side reactions of the nucleophilic secondary amines. In one embodiment, the cell permeable ATP analog has the following formula:

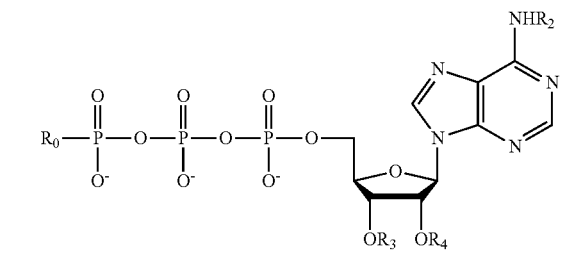

or a physiologically or pharmaceutically acceptable salt thereof, wherein:

$R_0$ is

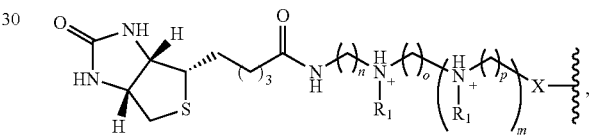

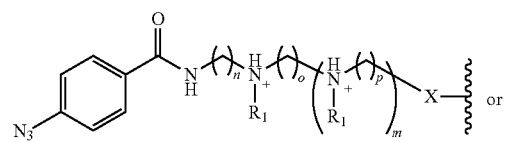

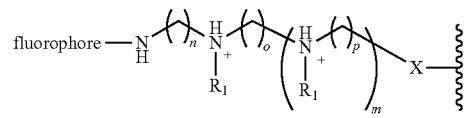

n, o, p are each independently 1, 2, 3, 4, 5, or 6;

m is 0, 1, 2, 3, 4, or 5;

X is O, S, NH, or $CH_2$;

$R_1$ is H or $C_{1-6}$ alkyl, $R_2$ is H, $C_{1-6}$ alkyl, $C_{6-30}$ aryl, $C_{5-32}$ heteroaryl, or $C_{7-32}$ alkylaryl;

$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

In another embodiment, a method of introducing a cell permeable ATP analog into a cell is provided. The method includes a step of contacting a cell from a subject with a cell permeable ATP analog having the following formula:

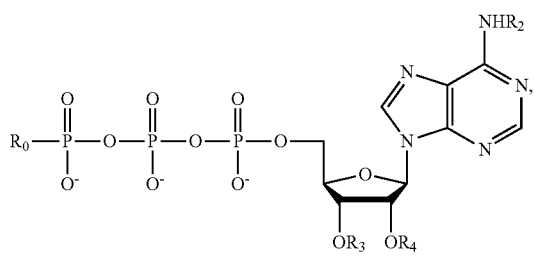

or a physiologically or pharmaceutically acceptable salt thereof,
wherein:

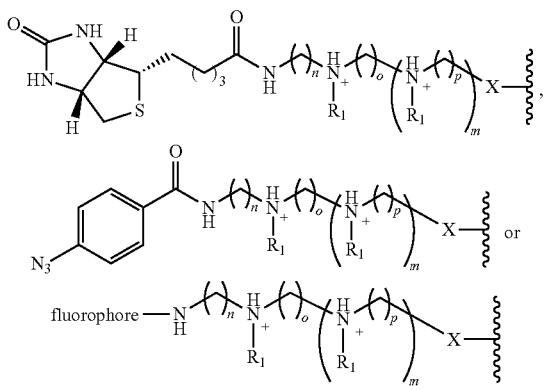

n, o, p are each independently 1, 2, 3, 4, 5 or 6;
m is 0, 1, 2, 3, 4, or 5;
X is O, S, NH, or $CH_2$;
$R_1$ is H or $C_{1-6}$ alkyl;
$R_2$ is H, $C_{1-6}$ alkyl, $C_{6-30}$ aryl, $C_{5-32}$ heteroaryl, or $C_{7-32}$ alkylaryl;
$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure. A determination is made if the cell permeable ATP analog has entered the cell with a portion of the cell permeable ATP analog having attached a protein substrate. A determination is made if the cell permeable ATP analog has entered the cell with a portion of the cell permeable ATP analog having attached a protein substrate or through fluorescence microscopy studies.

BRIEF DESCRIPTION OF THE DRAWINGS

FIGS. 2A and 2B. A) Docking of APB into the crystal structure of the catalytic active site of PKA kinase co-crystallized with peptide substrate (pdb: 4DH1) using Autodock 4.2. The arrow points to the solvent exposed biotin group. B) Enlarged view of the interaction of APB with the catalytic $Mg^{2+}$ metal (yellow orb) and amino acids K72 and K168. The γ-phosphate of APB is positioned in a close proximity to K168 while the α-phosphate lies near K72. The APB atoms are color-coded (C=green; H=grey; N=blue; O=red; P=orange). For clarity, the atomic radius of $Mg^{2+}$ was reduced to 0.5 Å.

FIGS. 3A and 3B. Kinase-catalyzed biotinylation with APB. A) Myelin basic protein (MBP) was incubated with or without PKA kinase in the presence of either ATP or APB. The labeling mixtures were separated by SDS-PAGE and visualized with SYPRO® Ruby total proteins stain (bottom), or streptavidin-Cy-5 (top). TFA (50% final concentration) was added after biotinylation labeling (lane 5). Full gel images are in FIG. 14B) Quantitative analysis of MBP phosphorylation was performed in the presence of PKA and ATP (lane 2), ATP-biotin (lane 3), or APB (lane 4). TFA was used to cleave the biotin group and produce the same phosphoprotein product with all analogs. The reaction mixtures were separated by SDS-PAGE and visualized with SYPRO® Ruby stain (bottom) or ProQ diamond phosphoprotein stain (top). The percentage phosphorylation was calculated by comparison with ATP (set as 100%). The gels are representative of at least three independent trials.

FIGS. 5A, 5B, 5C, and 5D. Docking of ATP-biotin (A) and ATP (B) into the crystal structure of the catalytic active site of PKA kinase (green) co-crystallized with peptide substrate (pdb: 4DH1)[6] using Autodock4.2[7]. The lowest energy binding pose is shown. An arrow points to the biotin group of ATP-biotin in part B. (C and D) An enlarged view of the interaction of ATP-biotin (C) and ATP (D) with the catalytic $Mg^{2+}$ metal (yellow orb) and amino acids K72 and K168 of PKA. The γ-phosphates of ATP-biotin and ATP are positioned in a close proximity to the co-crystallized peptide (A and B) and catalytic K168 (C and D). The atoms of ATP-biotin or ATP are color-coded (C=green; H grey; N=blue; O=red; p=orange). For clarity, the atomic radii of $Mg^{2+}$ were reduced to 0.5 Å in C and D.

FIGS. 17A, 17B, and 17C. Michaelis-Menton curve fits for reaction containing ATP (A) or APB (B) as the cosubstrate, with kinetic analysis comparison between ATP and APB in the table (C).

FIGS. 22A, 22B, and 22C. A) Fluorescence microscopy with DC. HeLa cells were incubated with ATP, ATP-biotin, DC, or the ATP-biotin/DC complex, followed by washing, fixing, and visualizing with streptavidin-Cy5 (SA-Cy5) to observe biotin (top) and DAPI to stain nuclear DNA (bottom). B) Fluorescence microscopy with digitonin. HeLa cells were incubated with digitonin or the ATP-biotin/digitonin complex, followed by washing, fixing, and visualizing with SA-Cy5 (top) and DAPI (bottom) C) MALDI monitoring of the permeability of the ATP-biotin/DC complex. HeLa cells were incubated with ATP-biotin, DC, or the ATP-biotin/DC complex, followed by analysis by MALDI-TOF MS. The ATP-biotin peak is at 934 m/z, whereas the 943 m/z peak is matrix contaminant.

FIGS. 23A, 23B, and 23C. A) DC-assisted in cellulo kinase-catalyzed biotinylation of HeLa cells with ATP-biotin or ATP-biotin/DC complex under normal growth conditions. As a control, HeLa cells were preincubated with kinase inhibitor staurosporine (STSP, lane 4). B) In vitro kinase-catalyzed biotinylation of HeLa lysates with ATP-biotin. As a negative control, ATP-biotin was incubated with heat-denatured (HD) HeLa cell lysates. C) Digitonin-assisted in cellulo kinase-catalyzed biotinylation of HeLa cells with ATP-biotin under normal growth conditions in either buffer or media. SDS-PAGE gel analysis was used to separate reaction mixtures and gels were visualized with streptavidin-Cy5 (top gels) or SYPRO® Ruby total protein stain (bottom gels). All images are representative of at least three independent trials (FIGS. 28 and 29).

FIGS. 24A, 24B, and 24C. A) Dose dependent assessment of cell viability with treatment of the ATP-biotin/DC complex (1 mM/0.9 mg/mL, 2 mM/1.88 mg/mL, 4 mM/3.75 mg/mL, 8 mM/7.5 mg/mL, or 10 mM/9.4 mg/mL). The box inset shows the fit of the data to a sigmoidal binding curve. B) The raw cell viability data at each ATP-biotin/DC complex concentration used to produced the plot in part A. C) Cell viability data of a ATP-biotin/digitonin mixture (4 mM/20 μg/mL) incubated either in P buffer or F-12 media. Mean and standard error of three independent trials are shown in both parts B and C.

FIGS. 28A, 28B, 28C, and 28D. Repetitive trials of in cellulo and in vitro DC-assisted biotinylation. A) In cellulo kinase-catalyzed biotinylation experiment of HeLa cells with ATP-biotin or ATP-biotin/DC complex. As a control, HeLa cells were preincubated with kinase inhibitor staurosporine (STSP) to prevent kinase catalysis. B) In vitro kinase-catalyzed biotinylation using ATP-biotin with HeLa cell lysates. As a negative control, ATP-biotin was incubated with heat-denatured HeLa cell lysates (HD lysates). SDS-PAGE gel analysis was used to separate reaction mixtures and gels were visualized with streptavidin-Cy5 (SA-Cy5, top gels) or SYPRO® Ruby total protein stain (bottom gels). The protein ladder contains proteins of the following sizes: 170, 130, 100, 72, 55, 43, 34, and 26 kDa.

FIGS. 30A and 30B. Digitonin-assisted pseudo in cellulo kinase-catalzyed labeling with ATP-biotin. Cells were harvested, permeabilized with digitonin, washed, and then incubated with ATP-Biotin (Lanes 4 and 8). As a control, harvested cells were preincubated with kinase inhibitor staurosporine (STSP) to prevent kinase catalysis (part A, lane 5). SDS-PAGE gel analysis was used to separate reaction mixtures and gels were visualized with streptavidin-Cy5 (top gel) or SYPRO® Ruby total protein stain (bottom gels). Two independent trials are shown here in parts A and B.

DETAILED DESCRIPTION

Figure 1A:
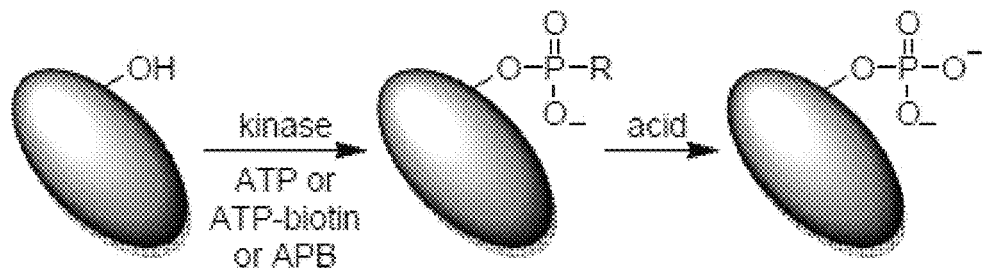
FIGS. 1A and 1B. (A) Kinase-catalyzed phosphorylation of a protein substrate (green) with (B) ATP (R=O—) or ATP analogs ATP-biotin (1), or APB (2).
Figure 1B:
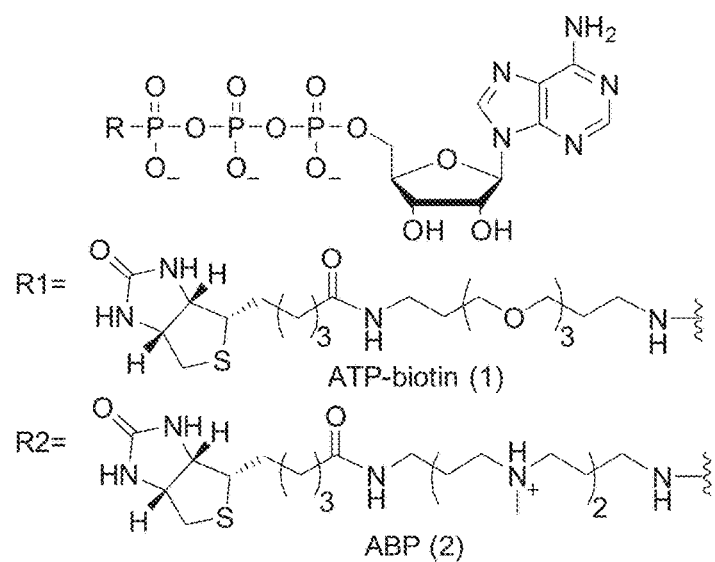

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include alkyl, lower alkyl, $C_{1-6}$ alkyl, $C_{6-10}$ aryl, or $C_{6-10}$ heteroaryl; single letters (e.g., "n" or "o") are 1, 2, 3, 4, or 5; percent, "parts of" and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, n-propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

The term "subject" refers to a human or animal, including all mammals such as primates (particularly higher primates), sheep, dog, rodents (e.g., mouse or rat), guinea pig, goat, pig, cat, rabbit, and cow.

The term "fluorophore" as used herein means a fluorescent chemical moiety that can re-emit light upon light excitation.

In an embodiment, the cell permeable ATP analog has the following formula:

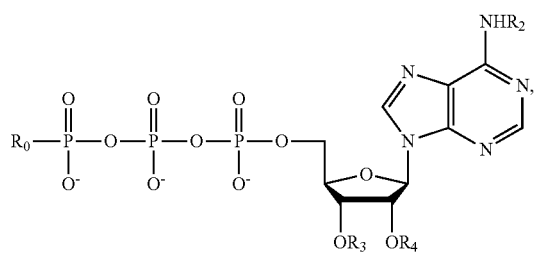

or a physiologically or pharmaceutically acceptable salt thereof,
wherein:
$R_0$ is

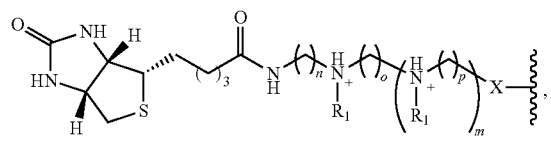

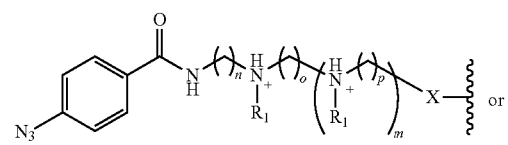

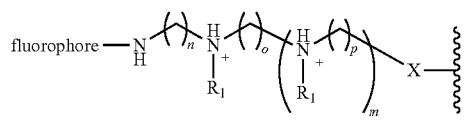

(squiggly lines indicate point of attachment).
n, o, p are each independently 1, 2, 3, 4, 5, or 6;
m is 0, 1, 2, 3, 4, or 5;
X is O, S, NH, or $CH_2$;
$R_1$ is H or alkyl (e.g., lower alkyl);
$R_2$ is H, alkyl (e.g., lower alkyl), $C_{6-30}$ aryl, $C_{5-32}$ heteroaryl, or $C_{7-32}$ alkylaryl;
$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure. In a refinement, $R_1$ is H or $C_{1-6}$ alkyl. In another refinement, $R_2$ is H, $C_{1-6}$ alkyl, $C_{6-30}$ aryl, $C_{5-32}$ heteroaryl, or $C_{7-32}$ alkylaryl. In another refinement, $R_1$ is H, methyl, ethyl, isopropyl, or propyl and $R_2$, $R_3$, $R_4$ are each independently H. In another refinement, $R_1$ is H or methyl and $R_2$, $R_3$, $R_4$ are each independently H. In particularly useful refinement, n is 3, o is 4, p is 3, and m is 1. Examples of fluorphores, include, but are not limited to, dansyl, fluorescein and its derivatives, cyanine dyes (for example, Cy3, Cy5, etc.), TAMRA and its derivatives, rhodamines and its derivatives, Alexa Fluor analogs, IR dyes, ATTO dyes, Texas Red, Oregon Green, coumarin, acridine dyes, BODIPY, and Qdot probes.

In a variation of the cell permeable ATP analogue, $R_2$ is methyl, ethyl, propyl,

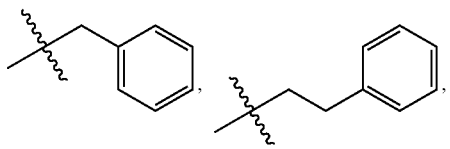

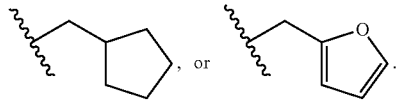

In another variation of the cell permeable ATP, $R_3$, $R_4$ are each independently H, methyl, ethyl, isopropyl, propyl,

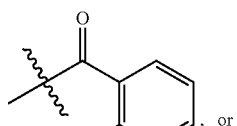

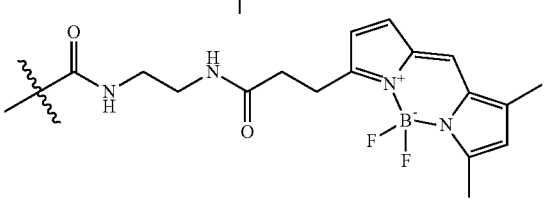

In another variation, the cell permeable ATP analog has the following formula:

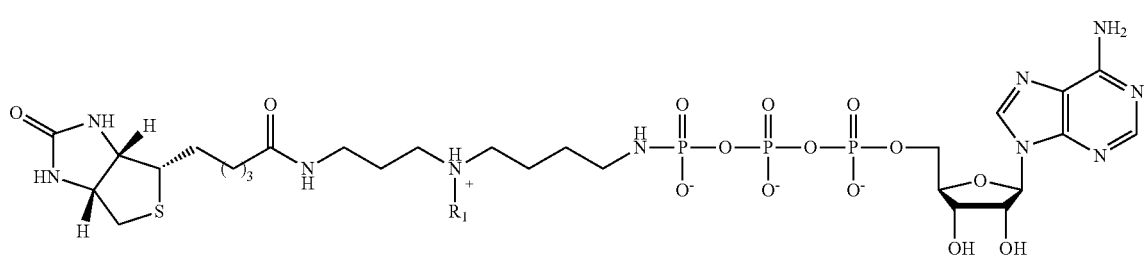

or a physiologically or pharmaceutically acceptable salt thereof. R1, R2, $R_3$, $R_4$ are as defined above.

In a particularly useful refinement, the cell permeable ATP analog of claim 1 has one of the following formulae:

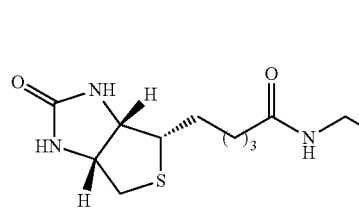
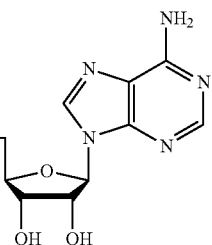

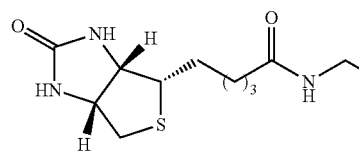
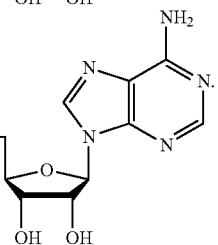

In a variation of the cell permeable ATP analog set forth above, the cell permeable ATP analog is combined with chitosan, and in particular, deacetylated chitosan to formed a ATP analogy/chitosan complex with improved permeability into living cells. In one refinement, the ATP analogy/chitosan complex is a particle typically having an average size of 100 to 1000 nm. In another refinement, the ATP analogy/chitosan complex is a particle typically having an average size of 200 to 600 nm.

In another embodiment, a method for introducing the cell permeable ATP analogs set forth above in a cell is provided. The method includes a step of contacting a cell from a subject with one or more of the cell permeable ATP analogs set forth above. In subsequent steps, a determination is made whether or not the cell permeable ATP analog has entered the cell with a portion of the cell permeable ATP analog having attached a protein substrate. Such a determination can be by affinity chromatography, antibodies, electrophoresis (e.g., SD-Page gel separation), and the like.

The following examples illustrate the various embodiments of the present invention. Those skilled in the art will recognize many variations that are within the spirit of the present invention and scope of the claims.

protrudes from the active site, while the triphosphate is positioned in a close proximity to the co-crystallized peptide. The α-phosphate of APB is 3.8 Å from the catalytic amino acid K72, as compared to 3.7 and 3.2 Å with ATP or ATP-biotin, respectively (FIGS. 5C and D), suggesting that the three ATP molecules bind similarly in the active site. In contrast, the γ-phosphate of APB is 3.9 Å from K168 (FIG. 2B), as compared to 2.4 Å with both ATP and ATP-biotin (FIGS. 5C and D). The docking studies suggest that APB is a potential kinase cosubstrate due to the similar active site binding. However, the long distance between the γ-phosphate of APB and K168 suggests that APB may be a less efficient cosubstrate compared to ATP or ATP-biotin.

To experimentally test APB as a kinase cosubstrate, it was first synthesized from commercially available spermine (Scheme 1). Spermine (3) was protected at the primary amines followed by reductive amination to give Boc-protected methylated spermine (4). After deprotection, the NETS-ester of biotin (FIG. 6) was synthesized as reported and coupled to give polyamine biotin (5). Finally, polyamine-biotin (5) was coupled with ATP to obtain APB (2).

Scheme 1

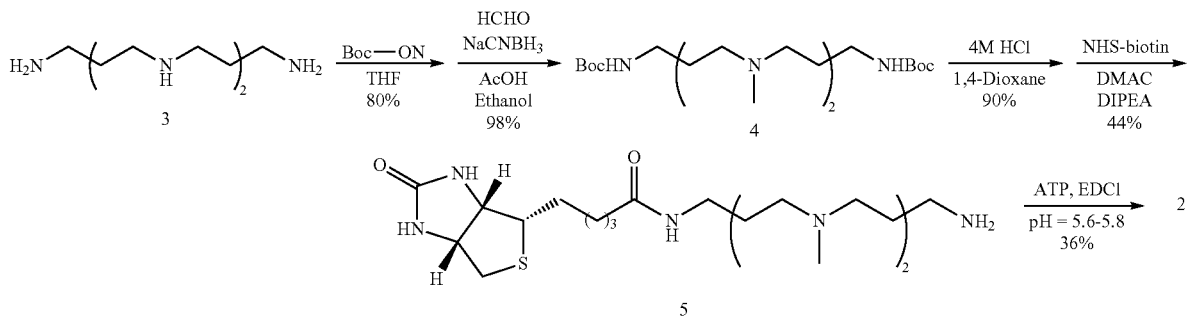

Figure 15A:
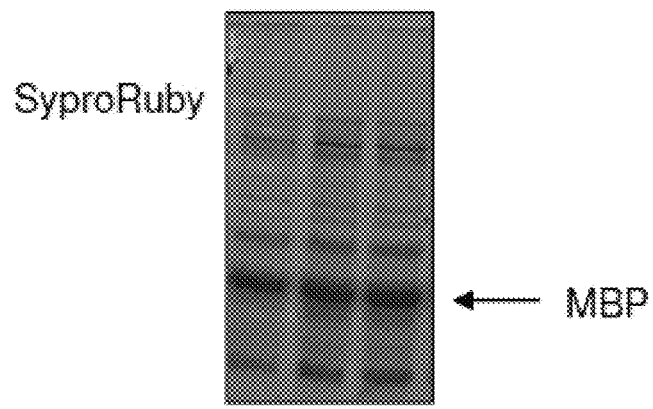
FIGS. 15A and 15B. Gel images of kinase-catalyzed biotinylation with MBP, PKA, and APB in presence and absence of 1 μM staursporine (STSP). The labeled mixtures were separated by SDS-PAGE and visualized by SYPRO® Ruby to observe total proteins (A) or streptavdine Cy-5 (SA-Cy5, Life Technologies) to detect biotinylation (B). The images are representative of at least three independent trials.
Figure 15B:
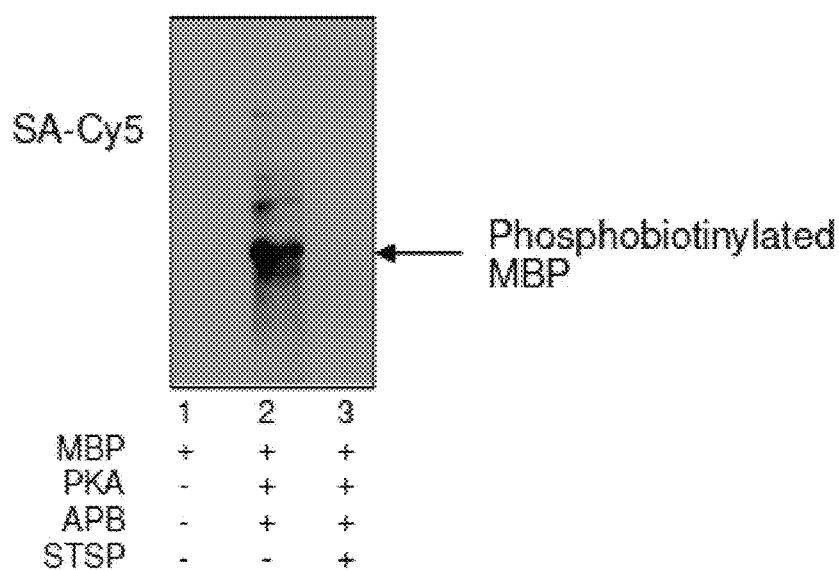
Figure 16A:
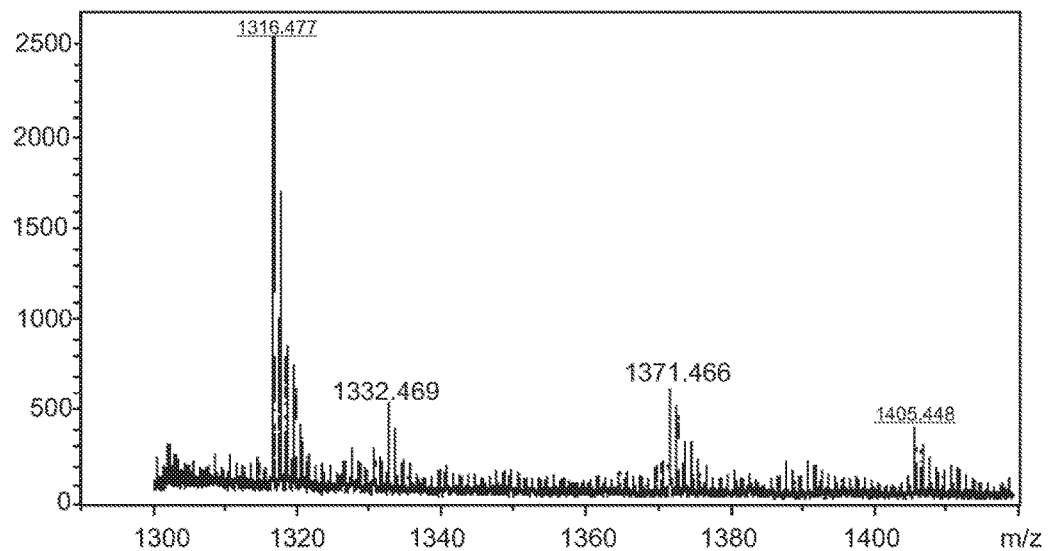
FIGS. 16A and 16B. MALDI-TOF spectra of a kinase-catalyzed phosphobiotinylation reaction of N-acetylated kemptide with PKA in positive ion mode. A) Reaction in the presence of APB: ([M+H]$^+$ for $C_{56}H_{107}N_{19}O_{14}PS$, Calculated: 1332.7698; Observed: 1332.469; [M+K]$^+$ for $C_{56}H_{106}KN_{19}O_{14}PS$, Calculated: 1371.7151; Observed: 1371.466 B) Reaction in the absence of APB showing no product peaks in the same m/z range.
Figure 16B:
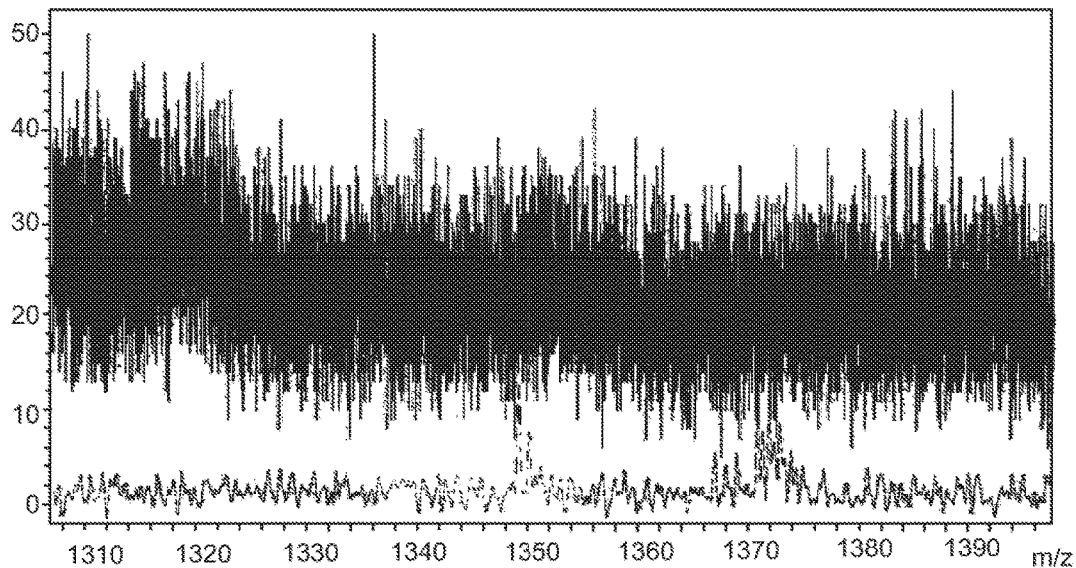

To computationally analyze the kinase compatibility of APB, docking studies with the PKA kinase crystal structure were performed using the Autodock program. Nearly identical PKA binding was observed with of APB (FIG. 2A), ATP-biotin (FIG. 5A), and ATP (FIG. 5B). The biotin group To test compatibility with kinase-catalyzed biotinylation, APB was incubated with PKA kinase and full-length protein substrate, myelin basic protein (MBP). Biotinylation was visualized after SDS-PAGE gel separation, transfer to PVDF membrane, and staining with a streptavidin-Cy5 conjugate (FIG. 3A). Biotinylation was observed only in presence of kinase (FIG. 3A, compare lanes 3 and 4). In addition, MBP biotinylation was lost in the absence of APB (FIG. 3A, lane 2), in presence of the kinase inhibitor staursporine (FIG. 15, compare lanes 2 and 3) or upon incubation with acid (FIG. 3A, lane 5) due to cleavage of phosphoramidate bond (FIG. 1A). To further confirm kinase-catalyzed biotinylation by APB, a mass spectrometric (MS) study was performed. In this case, the PKA peptide substrate kemptide was incubated with APB and PKA before MALDI-TOF MS analysis. Biotinylated kemptide product was observed only in the presence of APB cosubstrate (FIG. 16, m/z 1332.490 (M+H)$^+$). The combined gel and MS analyses confirm that APB is a kinase cosubstrate.

To investigate the efficiency of biotinylation using APB, both quantitative percentage conversion and kinetic studies were performed. For quantitative conversion studies, APB, ATP-biotin, and ATP were separately incubated with MBP and PKA, followed by cleavage of the phosphoramidate bond with acid to produce phosphoprotein products with all ATP analogs (FIG. 1A), which allowed quantitative comparison. The reaction mixtures were then separated by SDS-PAGE with phosphoproteins visualized by ProQ diamond stain (FIG. 3B), as previously reported. Quantification showed 55±6% conversion with APB compared to ATP (FIG. 3B, lane 4), while ATP-biotin showed 72±7% conversion compared to ATP (FIG. 3B, lane 3]. Biotinylation was less efficient with APB compared to ATP-biotin, as predicted by the docking studies. However, the observed quantitative analysis confirmed that APB is a kinase cosubstrate. Next, kinetic studies were performed by incubating APB or ATP (0.5-100 µM) with PKA and kemptide peptide substrate. APB showed a reduced $k_{cat}/K_M$ (0.25 s$^{-1}$ µM$^{-1}$) compared to ATP (0.52 s$^{-1}$ µM$^{-1}$) (FIG. 17). However, the kinetics are similar to those observed with other ATP analogs used for kinase studies, including the γ-phosphate modified ATP analog ATP-dansyl, or the base-modified analogs N$^6$-benzyl ATP or N$^6$-(2-phenethyl) ATP. In total, both quantitative conversion and kinetics studies confirm that APB is an efficient kinase cosubstrate with conversions and kinetics similar to other known ATP analogs.

Figures 4A, 4C:
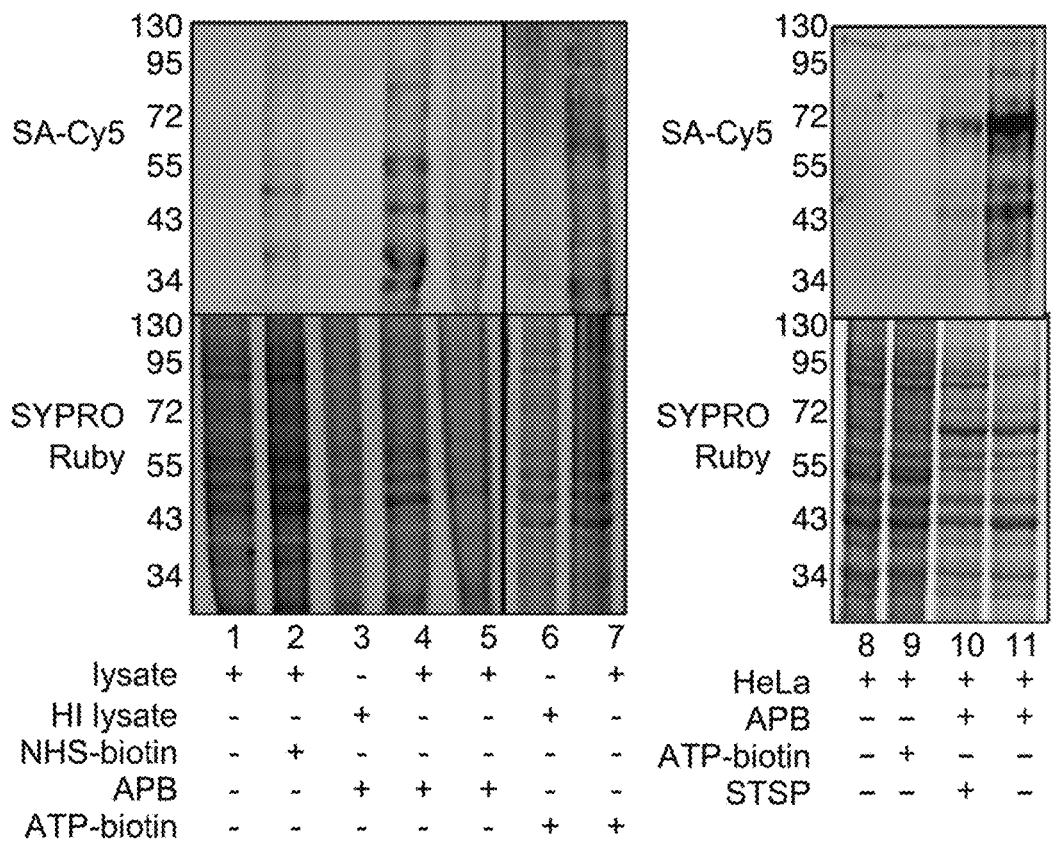
FIGS. 4A, 4B, and 4C. A) Kinase-catalyzed biotinylation of HeLa cell lysates (lysate) or heat-inactivated Hela cell lysates (HI lysate) with APB and ATP-biotin. Acid (50% trifluoroacetic acid final concentration) was added after biotin labeling to cleave the biotin tag (lane 5). NHS-biotin (FIG. 6) was used to assess nonspecific biotinylation. B) Fluorescence microscopy images of Hela cells after treatment with ATP, ATP-biotin, or APB, fixation, and visualization with SA-Cy5 for detection of biotin (red). Enlarged images and DAPI nuclear staining are shown in FIG. 18C) In cellulo kinase-catalyzed biotinylation with ATP-biotin or APB in HeLa cells. As a control, kinase inhibitor staurosporine (STSP) was pre-incubated with cells to prevent kinase catalysis (lane 3). Reaction mixtures (A and C) were separated by SDS-PAGE and visualized with streptavidin-Cy5 (SA-Cy5, top gel) or SYPRO® Ruby total protein stain (bottom gels). The gels are representative of at least three independent trials.

To analyze the compatibility of APB with cellular kinases, HeLa cell lysates were incubated with APB, followed by SDS-PAGE analysis. Biotinylation of proteins was detected in the APB reaction (FIG. 4A, lane 4), showing the promiscuity of cellular kinases for APB. Similar levels of labeling were observed comparing APB and ATP-biotin (FIG. 4A, lane 4 versus 7). As a control, heat denatured lysates generated low levels of biotinylation with both APB and ATP-biotin (FIG. 4A, lanes 3 and 6), which confirmed the kinase-dependence of biotinylation. Acid treatment also reduced biotinylation (FIG. 4A, lane 5), which indicated labeling via the phosphoramidate bond in APB (FIG. 1A). These studies in lysates further establish the compatibility of APB with a range of cellular kinases and substrates, similar to ATP-biotin.

Figure 4B:
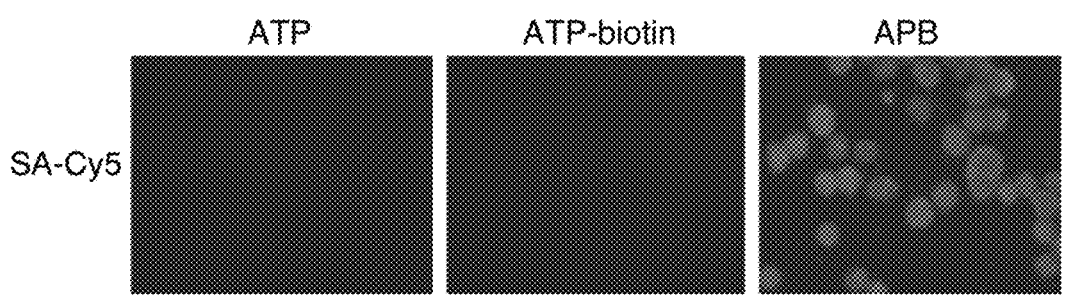
Figure 18:
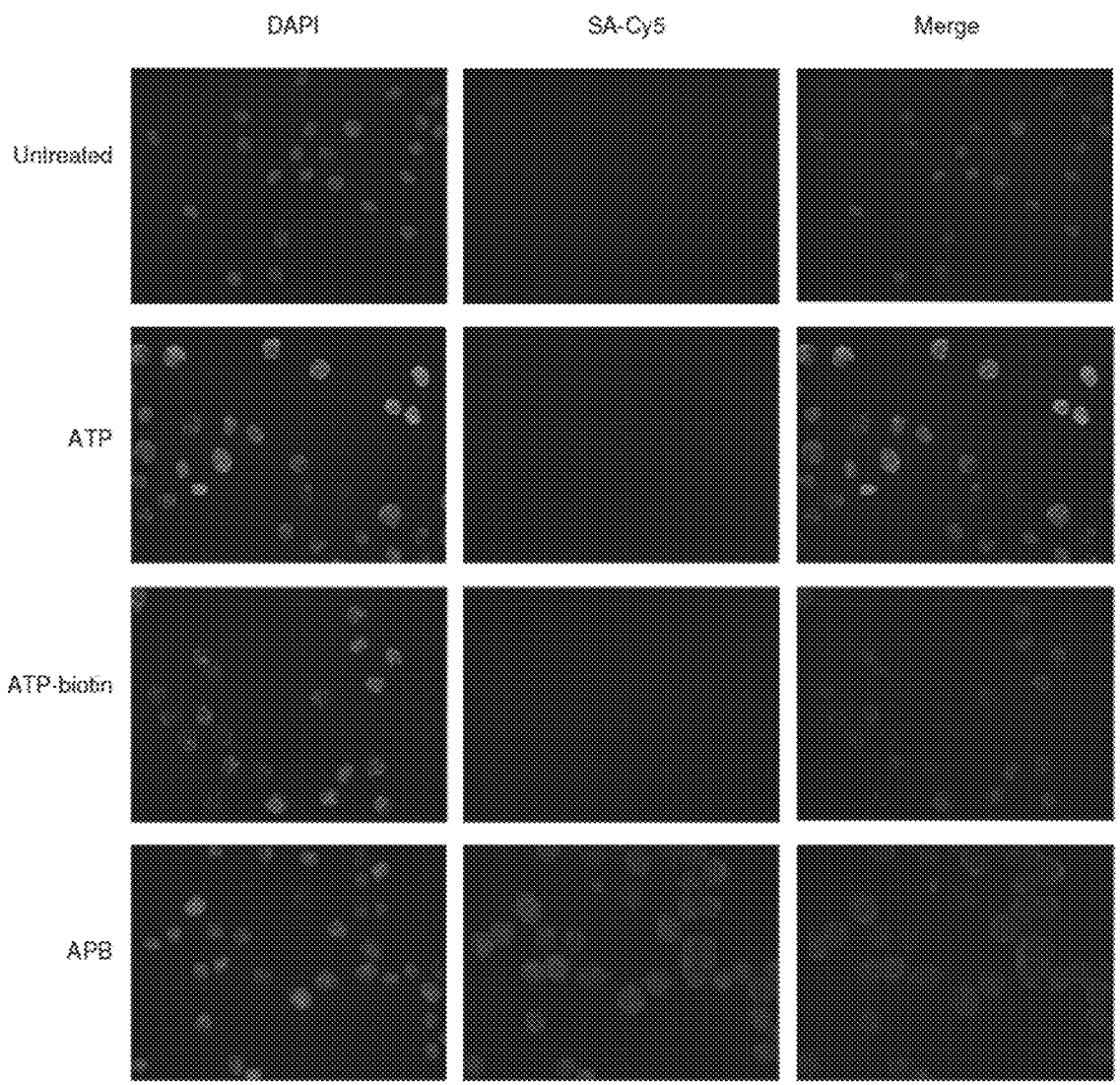
FIG. 18. Microscopy studies of ATP-biotin or APB cell permeability. HeLa cells were untreated or treated with ATP, ATP-biotin or APB before visualization with the nuclear stain DAPI or biotin stain streptavidin-Cy5 (SA-Cy5). The merged images of DAPI and SA-Cy5 show that APB is found in both the nucleus and cytoplasm. This figure includes enlarged images also shown in FIG. 4C.

Having confirmed the kinase compatibility of APB in vitro, kinase-catalyzed biotinylation of live cells were tested. As a first step, fluorescence microscopy was used to confirm the cell permeability of APB. Hela cells were incubated with APB, followed by washing, fixation, and visualization with streptavidin-Cy5 to observe biotin. Cells treated with APB showed fluorescence corresponding to the presence of biotin (FIG. 4B). As controls, untreated cells (FIG. 18) or cells incubated with ATP or ATP-biotin showed no biotin signal (FIG. 4B), which indicated that the polyamine linker in APB was required to promote cell permeability. These microscopy studies confirm that APB is cell permeable and validate the use of a polycationic groups to enhance the permeability of ATP analogs.

Figure 19A:
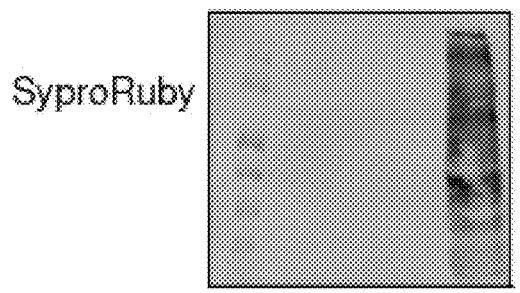
FIGS. 19A and 19B. Gel images of kinase-catalyzed biotinylation of live HeLa cells with impermeable ATP-biotin analog (4 mM final concentration) in presence and absence of exogenous HeLa lysates (80 μg), which contain kinase activity. As a control for the presence of cell surface proteins, HeLa cells were incubated with NHS-biotin (FIG. 6, 1 mM final concentration, lane 4). The cells were washed, lysated, and protein mixtures were separated by SDS-PAGE and visualized by SYPRO® Ruby to observe total proteins (A) or streptavdine Cy-5 (SA-Cy5, Life Technologies) to detect biotinylation (B). Biotin signal is absent with ATP-biotin in the presence or absence of the kinase activity in lysates (panel A, lanes 2 and 3), indicating no biotinylation of cell surface proteins. The images are representative of at least three independent trials.
Figure 19B:
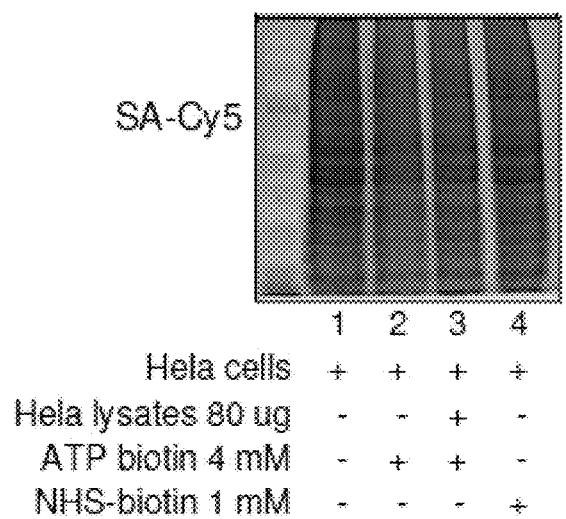
Figures 20A, 20B:
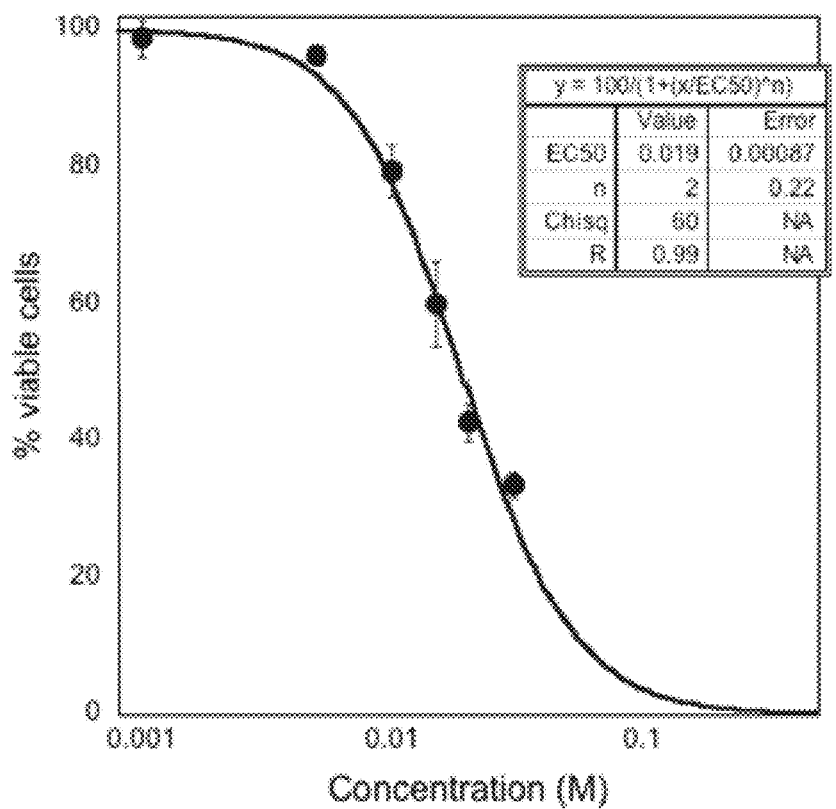
FIGS. 20A and 20B. Cell viability assays with varying concentrations of APB. A) Dose response curve of APB with 1, 5, 10, 15, 20, 30 mM final concentrations. The $EC_{50}$ of APB is 19±1. B) Table with the percentage viability data plotted in part A. The concentration of APB used in kinase-catalyzed labeling of cells was 5 mM.

With the cell permeability of APB confirmed, live cell biotinylation with ABP was performed. HeLa cells were incubated with APB, washed to remove excess analog, lysed, and then analyzed by SDS-PAGE. Cells incubated with APB showed protein biotinylation (FIG. 4C, lane 11), which is consistent with cell permeability. Biotinylation was absent with ATP-biotin under the same conditions (FIG. 4C, lane 9), further confirming that the polyamine linker is necessary to enhance cell permeability. Also, pre-treating cells with the kinase inhibitor staursporine reduced biotinylation (FIG. 4C, lane 10), indicating that the labeling is kinase-dependent. As a final control, ATP-biotin was incubated with HeLa cells in the presence of lysates containing kinase activity and no biotin signal was observed (FIG. 19A), which assures that biotinylation is independent of cell surface protein labeling. Treatment with APB was accompanied by a modest loss of total protein (FIG. 4C, lane 10 and 11, bottom gel) compared with controls (FIG. 4C, lane 8 and 9, bottom gel), which is similar to the levels of protein loss observed in previous cell permeability studies, including experiments with the widely used cationic-based permeabilization reagents. To assess APB cytotoxicity, a dose-dependent cell viability assay was performed. APB showed a cytotoxicity EC$_{50}$ value of 19±1 mM (FIG. 20A). Importantly, 96±1% cell viability was observed with the 5 mM concentration of APB used in the cell labeling assay (FIG. 20B). The cell-based studies show that APB is cell permeable and nontoxic at low mM concentrations, with cell penetration and labeling dependent on the polyamine linker.

Figure 6:
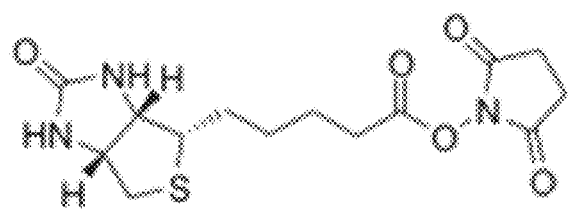
FIG. 6. The structure of NHS-biotin used in the synthesis of APB and studies in FIG. 4.
Figure 7:
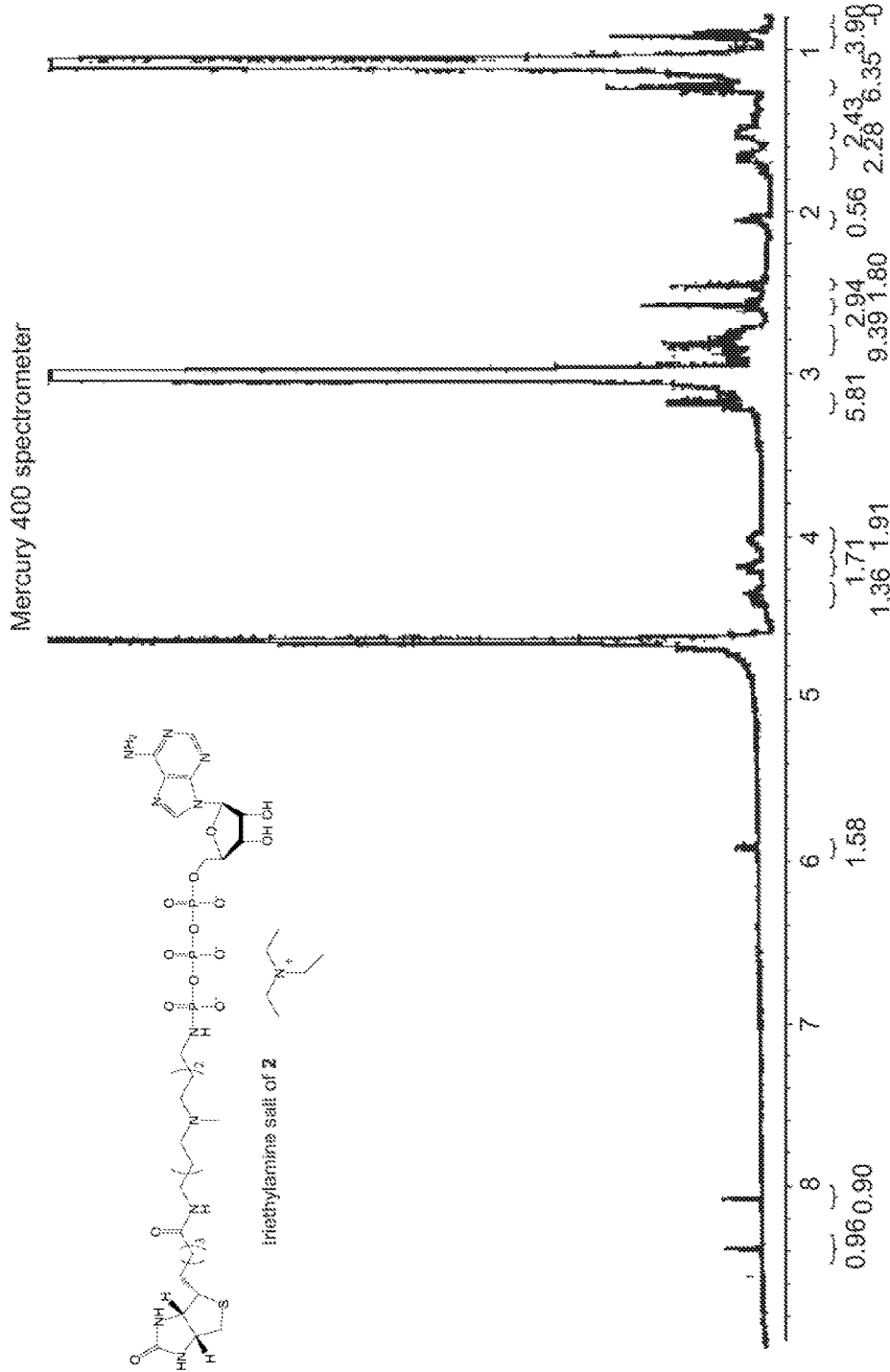
FIG. 7. $^1H$ NMR of the triethyl amine salt of ATP-polyamine-biotin (ABP) recorded in $D_2O$ at 400 MHz.
Figure 8:
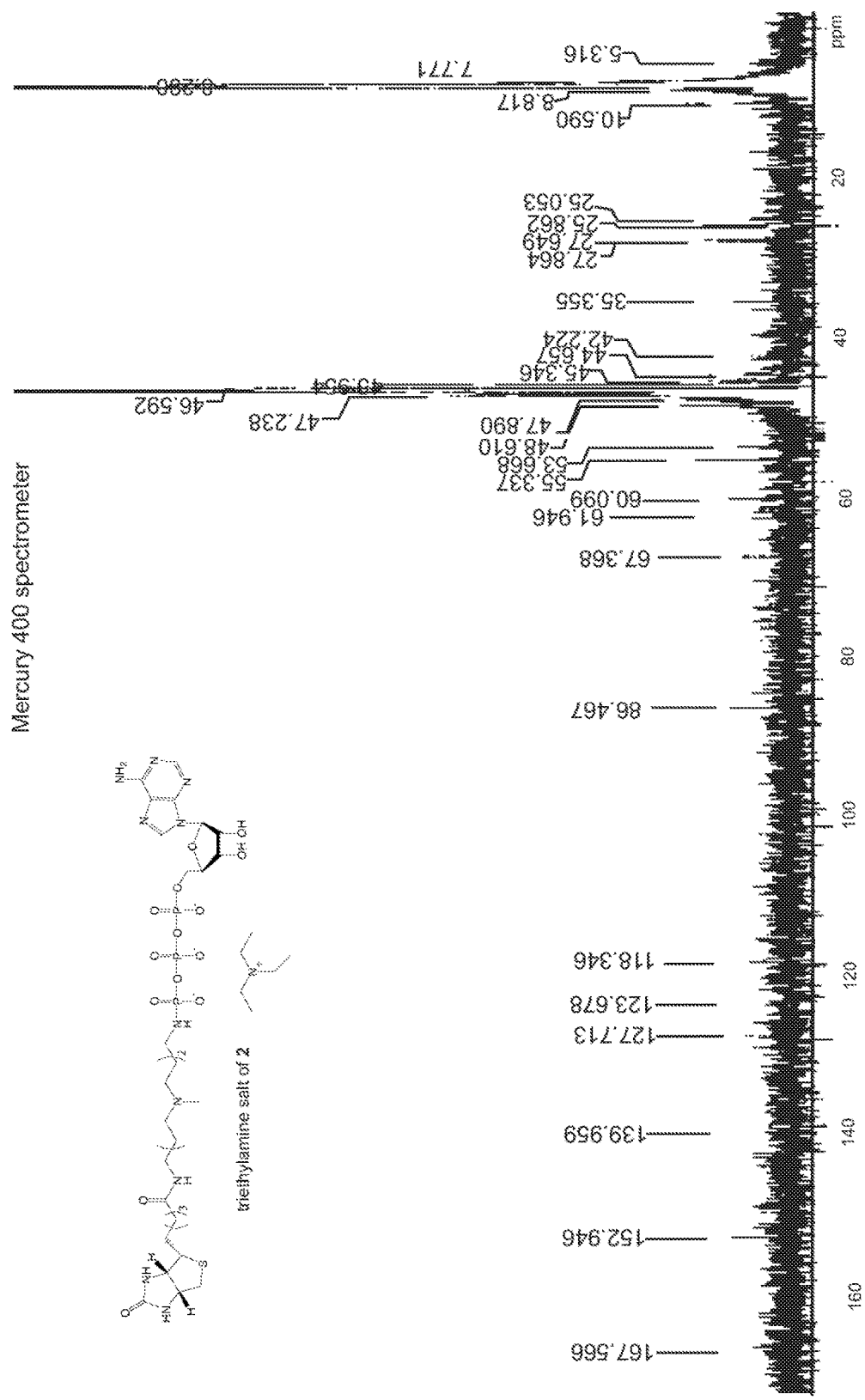
FIG. 8. $^{13}C$ NMR of the triethyl amine salt of ATP-polyamine-biotin (ABP) recorded in $D_2O$ at 100 MHz.
Figure 9:
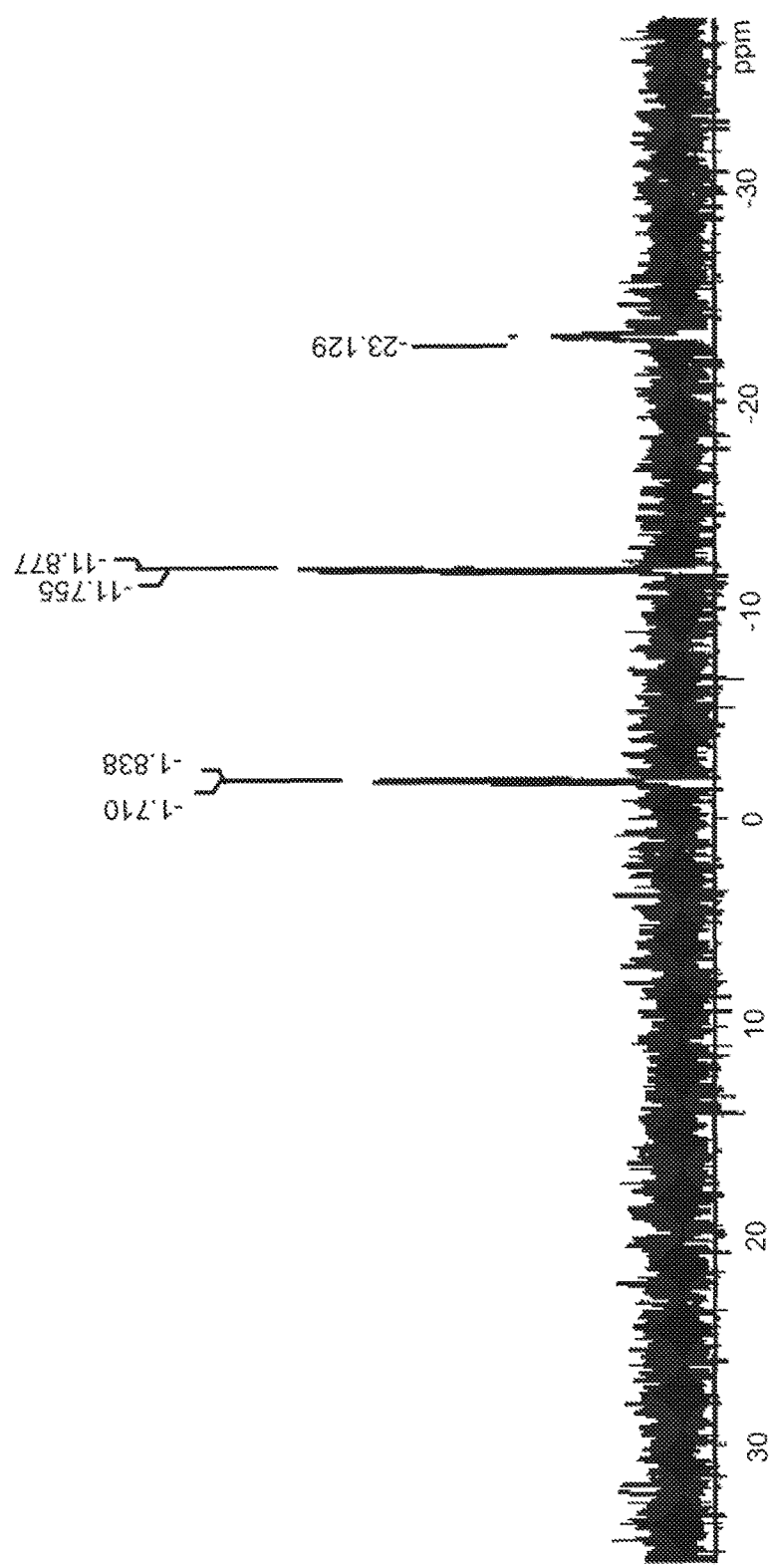
FIG. 9. $^{31}P$ NMR of the triethylamine salt of ATP-polyamine-biotin (ABP) recorded in $D_2O$ at 162 MHz.
Figure 10:
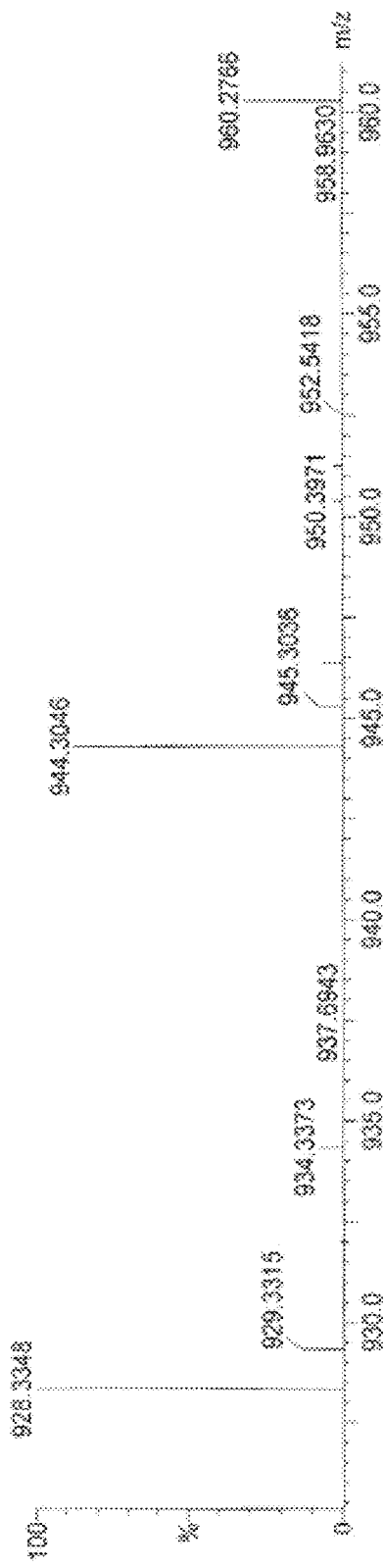
FIG. 10. Electrospray ionization (ESI) negative mode high resolution mass spectrum (HRMS) of ATP-polyamine-biotin (ABP) recorded in acetonitrile. Calculated $[M-H]^{-1}$ for $C_{32}H_{58}N_{11}O_{14}P_3S$: 944.3098; Observed: 944.3046
Figure 11:
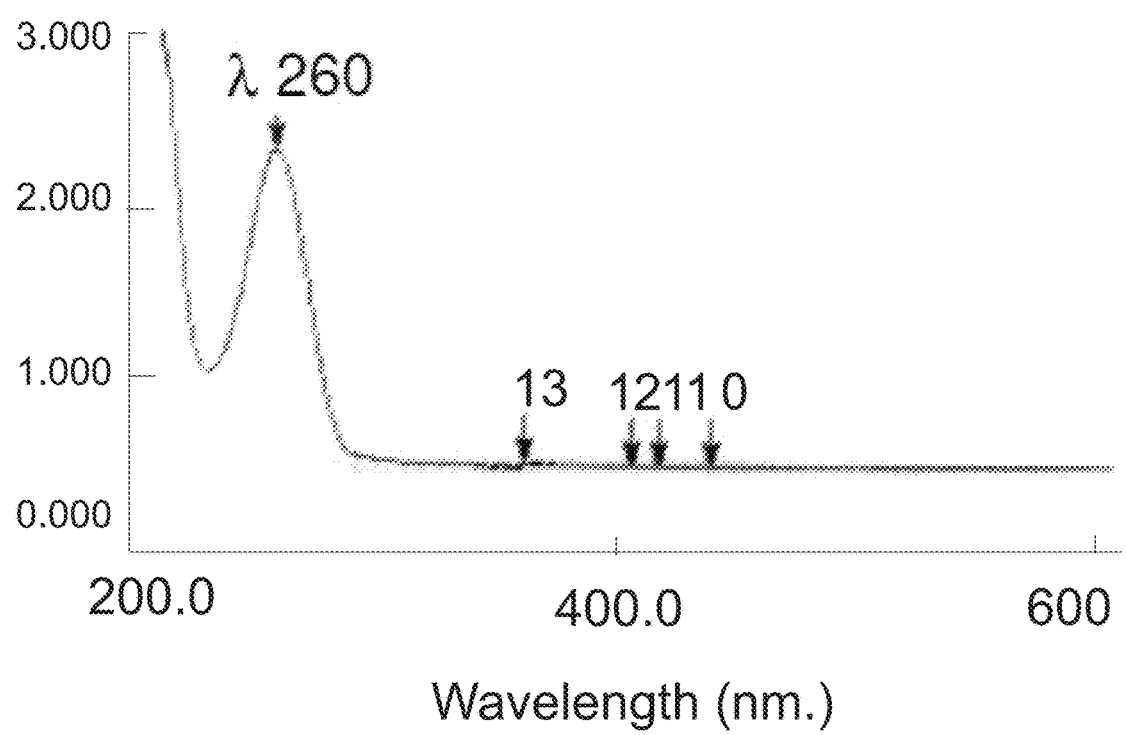
FIG. 11. UV-VIS spectrum of ATP-polyamine-biotin (ABP) recorded in water. The ABP absorbance appears at λ 260 nm FIG. 12. HPLC analysis of ATP-polyamine-biotin (ABP) purity. ATP-polyamine-biotin appears at 27.511 minutes and is 95% pure.
Figure 12:
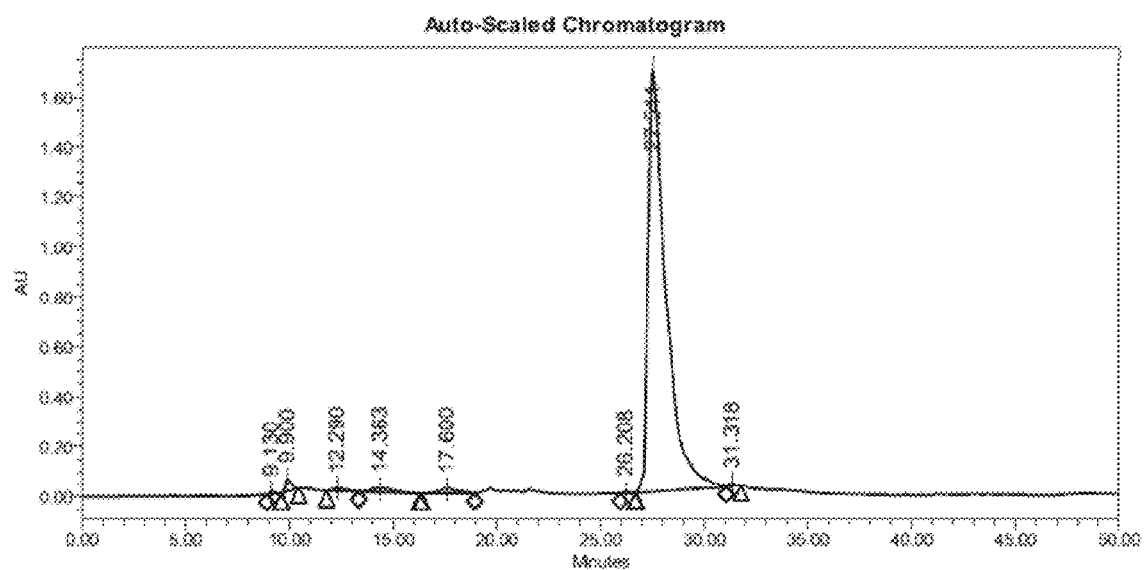
Figure 13:
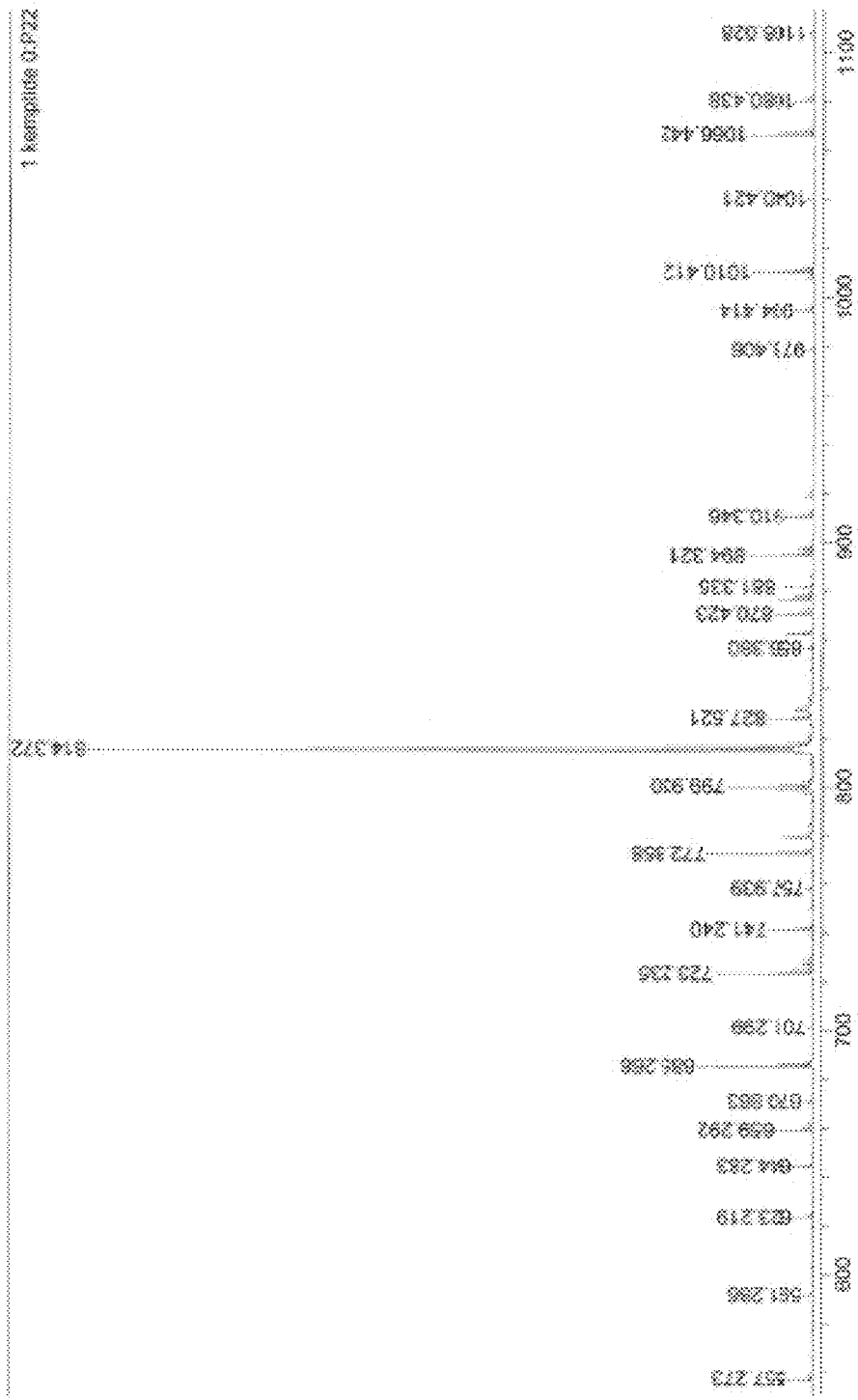
FIG. 13. MALDI-Tof positive mode of N-acetylated kemptide peptide (AcLRRASLG). Calculated [M+H]$^{+1}$ for $C_{34}H_{63}N_{13}O_{10}{}^+$: 814.4894; Observed: 814.372
Figure 14A:
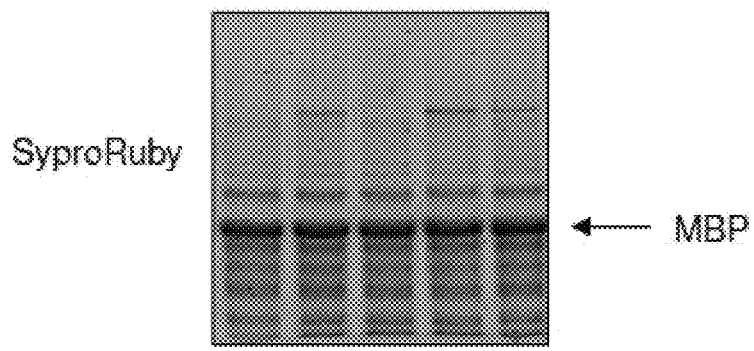
FIGS. 14A and 14B. Full gel images of kinase-catalyzed biotinylation with MBP, PKA, and APB, which is shown in FIG. 3A. The labeled mixtures were separated by SDS-PAGE and visualized by SYPRO® Ruby to see total proteins (A) or streptavdine Cy-5 (SA-Cy5, Life Technologies) to detect biotinylation (B). TFA (50%) was added after biotinylation labeling to assure biotinylation via an acid-labile phosphoramidate bond (lane 5). The images are representative of at least three independent trials.
Figure 14B:
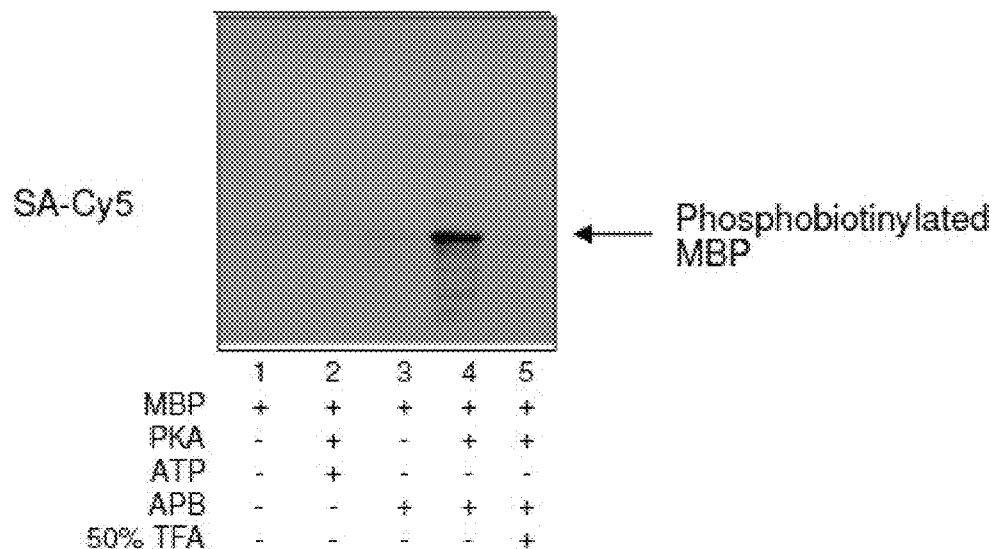

To assess the quality of biotinylation in the various labeling reactions, lysates were incubated with the non-specific biotinylation reagent, NHS-biotin (FIG. 6). Different biotinylated protein bands were observed with NHS-biotin treatment compared to kinase-catalyzed reactions with APB or ATP-biotin (FIGS. 4A and C, compare lane 2 to lanes 4, 7 and 11), suggesting kinase-selective biotinylation of both lysates and cells. Importantly, a comparison of APB labeling reactions in lysates and cells revealed different biotinylated protein products (FIGS. 4A and C, lanes 4 versus 11), which indicated that in cellulo labeling is distinct from labeling in lysates. We speculate that the difference in live cell versus lysates labeling may be due to compartmentalization inside the cell, which suggests that in cellulo labeling studies will better interrogate the phosphoproteome for cell signaling studies.

From these results, it is clear that embodiments of the invention provide the first cell permeable ATP analog compatible with kinase-catalyzed biotinylation. APB acted as a cosubstrate with protein kinases in vitro and in cellulo. While the percentage conversion and kinetic efficiency was reduced compared to ATP or ATP-biotin in vitro, APB was able to label phosphoproteins in live cells. Importantly, different biotinylated proteins were observed with in cellulo compared to lysate studies, which argue that labeling in cellulo will better reflect the cellular phosphoproteome. These results lay the foundation for future work using APB and kinase-catalyzed biotinylation as tools to identify and isolate phosphoproteins from cells, which will enhance cell signaling research.

Experimental Section

APB (2) was synthesized and characterized by $^1$H, $^{13}$C, and $^{31}$P NMR spectroscopy, UV spectroscopy, ESI mass spectroscopy, and MALDI spectrometry, as discussed in the supporting information (FIGS. 7-12). For in cell kinase-catalyzed biotinylation, Hela cells were grown in 12 well plates for 2 days in growth media (F-12 containing 10% FBS, 9 units penicillin, and 9 units streptomycin). The growth media was removed, replaced with fresh growth media containing APB (5 mM) or ATP-biotin (5 mM), and incubated at 37° C. for 1 hour in a $CO_2$ incubator to allow kinase-catalyzed labeling. As a control, staurosporine (1 μM) in fresh growth media was added to the cells for one hour before adding APB. After washing the cells, the reaction mixtures were separated by SDS-PAGE and visualized with SYPRO® Ruby total protein stain. Where indicated, the gel was stained with ProQ Diamond Phosphoprotein stain (Invitrogen), or the proteins were transferred onto a PVDF membrane (Immobilon-P, Milipore) and visualized with streptavidin-Cy5 reagent (Life Technologies) to detect biotinylated proteins. Detailed experimental procedures and data are supplied as supporting information.

1. Materials

Spermine, pyruvate kinase/lactate dehydrogenase, NADH, phosphoenol pyruvic acid and alpha-cyano-4-hydroxycinnamic acid were purchased from Sigma Aldrich. ATP was purchased from MP Biomedicals. Dimethyl acetamide (DMAC), 2-(tert-butoxycarbonyloxyimino)-2-phenylacetonitrile (Boc-ON), 1-(3-Dimethylaminopropyl)-3-ethylcarbodiimide hydrochloride (EDCI), N-hydroxy succinimide (NETS), and N,N,N',N'-Tetramethylethylenediamine for electrophoresis were purchased from Acros. The NHS-biotin ester was synthesized according to prior literature.[1] Sodium cyanoborohydride, formaldehyde, silica, DEAE sephadex A-25, and Ammonium persulfate (APS) for electrophoresis were bought from Fisher Scientific. Dichloromethane (DCM), acetic acid, hydrochloric acid, ammonium hydroxide, and HPLC grade acetonitrile were purchased from EMD. Ethanol was obtained from Decon lab. 40% Bis-acrylamide (37.5:1) for gel electrophoresis and Bradford reagent were purchases from Biorad. Myelin basic protein (MBP), F-12 media and trypan blue were bought from Invitrogen. PKA kinase was purchased from New England Biolabs. Antibiotic and Dulbecco's Phosphate Buffered Saline (DPBS) for cell culture were purchased from HyClone. 3-Hydroxypicolinic acid was bought from Fluka.

2. Instruments $^1$H NMR, $^{13}$C NMR, $^{31}$P NMR (Varian Mercury-400), and High resolution mass spectra (HRMS) (LCT Premier XT (Waters) were used to characterize the final APB analog. $D_2O$ was observed at δ 4.63 in $^1$H NMR. The peaks at δ 1.08 (t) and 3.01 in $^1$H NMR, and δ 8.29 and 46.59 in $^{13}$C NMR corresponded to the triethylamine counter ion. Absorbance of APB was measure by UV-Vis spectrophotometer (Shimadzu 2101 PC). A Lyophilizer (VirTis BT 3.3 EL Benchtop) and Speed-vac (ThermoSAVANT, SPD131 DDA) were used during synthesis of APB. RP-HPLC was performed with Waters 1525 binary HPLC pump, Waters 2998 photodiode array detector, and Reverse phase C-18 column (YMC America, INC 250×4.6 mm, 4 μm, 8 nm). Bradford assay was done using a fluorimeter (GENios Plus Tecan). SDS-PAGE apparatus were bought from BioRad (Protean III).

Protein transfer was performed using the Mini-Transblot Electrophoretic Transfer Cell apparatus from BioRad. SDS gels and PVDF membranes were visualized by a Typhoon 9210 scanner (Amersham Biosciences). Immunofluorescence images were visualized by Olympus fluorescence microscope (Model BX 41). Peptide masses was detected using MTP Plate (Bruker) and MALDI-TOF (Bruker Ultraflex).

3. Docking Studies

The crystal structure of PKA was downloaded from RCSB Protein Data Bank (pdb ID: 4DH1). The co-crystallized peptide, ATP, and water were deleted using Pymol 1.5.0.5 (Schrodinger, LLC). All hydrogen atoms, Gasteiger charges and merging non polar hydrogen were added by AutoDock Tools 1.5.6, followed by generation of pdbqt output file. The charge of Mg was changed from zero to +2 manually. A grid box with a spacing of 0.375 Å, size of 74×70×70, and coordinates for the center of the grid box (−9.145, 13.434, −21.018) were used. The grid map files required for docking calculations were generated by AutoGrid 4.2. APB was drawn in ChemBioDraw Ultra and MM2 energy minimization was done by Chem 3D Pro. AutoDock Tools 1.5.6 was used again to add hydrogens, compute Gasteiger charges, merge nonpolar hydrogens, choose torsions, and generate a pdbqt file. All acyclic bonds were rotatable except amide bonds. We then used AutoDock 4.2 to run docking calculations using the genetic algorithm, and a pdbqt file was generated. The pdbqt file for PKA was set as a rigid macromolecule and the genetic algorithm search parameters were set to 100 GA runs with a population size of 150, a maximum number of $2.5 \times 10^5$ energy evaluations, a maximum number of $2.7 \times 10^4$ generations, a mutation rate of 0.2, and a crossover rate of 0.8. Default docking parameters were used and the output DLG file was converted to pdbqt extension. PyMOL 1.5.0.5 (Schrodinger, LLC) was used to create images in FIGS. 2 and S1.

4. Synthesis of ATP-Polyamine-Biotin (ABP)

Amine-Protection of Spermine: Synthesis of di-tert-butyl ((butane-1,4-diylbis(azanediyl))bis(propane-3,1-diyl))dicarbamate (3a)

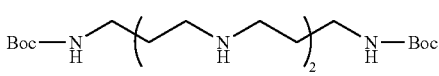

3a

Compound 3a was synthesized according to literature as follows. (Garcia, J.; Pereira, R.; de Lera, A. R., Total synthesis of the natural isoprenylcysteine carboxyl methyltransferase inhibitor spermatinamine. Tetrahedron Letters 2009, 50 (35), 5028-5030; the entire disclosure of which is hereby incorporated by reference). Spermine (3, 1 g, 4.9 mmol) was dissolved in THF (15 mL) at 0° C. A solution of BOC—ON (2.42 g, 9.8 mmol) in THF (30 mL) was added drop wise under argon at 0° C. After stirring at 0° C. for 2 minutes, the solution was stirred at room temperature for 1 hour. The reaction was quenched with saturated sodium carbonate (45 mL) and extracted with dichloromethane (135 mL). The organic layer was evaporated in vacuo and then the residue was purified by chromatography using silica and 5% ammonia in ethanol as eluting solvent to obtain 3a as a white solid (1.7 g, 80% yield). Spectral characterization was consistent with prior literature. (Garcia et al.).

Synthesis of di-tert-butyl ((butane-1,4-diylbis(methylazanediyl))bis(propane-3,1-diyl))dicarbamate (4)

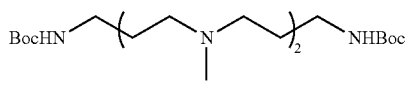

4

Compound 4 was synthesized according to literature. (Garcia et al.). Compound 3a (1.7 g, 3.9 mmol) was dissolved in ethanol (45 mL) together with a 37% formaldehyde solution (17.3 mL, 213.1 mmol). Acetic acid (11.5 mL) was added, followed by sodium cyanoborohydride (4.3 g, 68.4 mmol). The reaction was stirred overnight and then quenched with saturated sodium carbonate solution until effervescence ceased, followed by extraction with dichlormethane (3 times). The organic layer was evaporated in vacuo. The residue was purified by chromatography using silica and 5% ammonia in ethanol as eluting solvent to obtain 4 as yellowish oil (1.8 mL, 98% yield). The spectral characterization was consistent with prior literature. (Garcia et al.).

Synthesis N1,N1'-(butane-1,4-diyl)bis(N1-methylpropane-1,3-diamine) (4a)

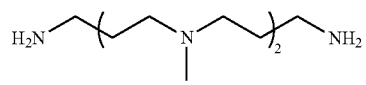

4a

Compound 4a was synthesized according to literature. (Garcia et al.). Compound 4 (1.83 g, 4.2 mmol) was dissolved in 1,4-dioxane (40 mL) at 0° C., followed by addition of 4N HCl (40 mL). The reaction was stirred at room temperature for 4 hours and then the solvent was evaporated in vacuo. The residue was crystallized with methanol/ethylacetate to give white crystals of compound 4a as a chloride salt (1.3 g, 90% yield). The spectral characterization was consistent with prior literature. (Garcia et al.).

Synthesis of Polyamine-Biotin (Using Methylated Spermine) (5)

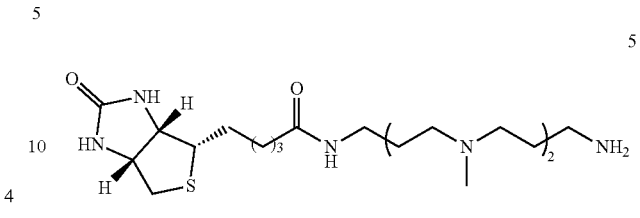

5

Polyamine-biotin (5) was synthesized according to literature with some modifications to the procedure. (Albarella, J. P.; Minegar, R. L.; Patterson, W. L.; Dattaguptal, N.; Carlson, E., Monoadduct forming photochemical reagents for labeling nucleic acids for hybridization. *Nucleic acid research* 1989, 17 (11), 4293-4308; the entire disclosure of which is hereby incorporated by reference). Methylated spermine (4a) (0.78 g, 2.5 mmol) was dissolved in a mixture of DMAC (25 mL) and DIPEA (3.3 mL) at 0° C. A solution of NHS biotin ester (350 mg, 1 mmol) in DMAC (30 mL) was added dropwise over an hour under argon and the reaction mixture was stirred overnight at room temperature, followed by addition of diethyl ether to precipitate the product. The precipitate was filtered and then purified by chromatography using silica and ethanol:THF:DCM:ammonia (4:4:2:1) as an eluting solvent. Polyamine-biotin (5) was obtained as oil (0.5 g, 44%). The spectral data was consistent with literature. (Albarella et al.)

Synthesis of ATP-Polyamine-Biotin (ABP, 2)

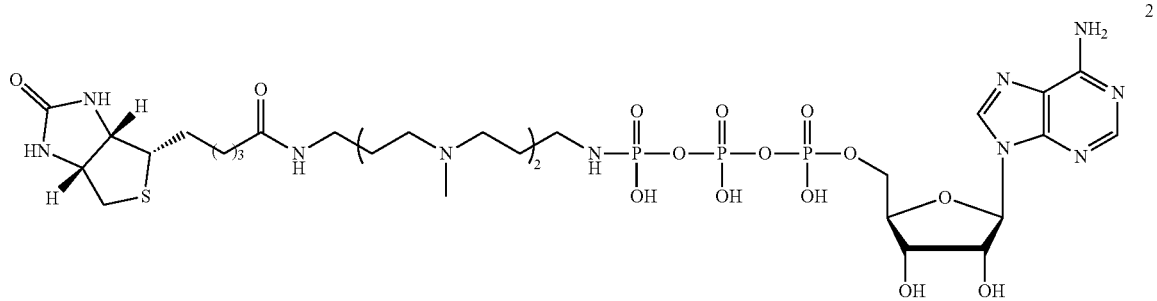

2

The disodium salt of ATP (32 mg, 0.059 mmol) was dissolved in water (5 mL) and then the pH was adjusted to 7.0 with NaOH (0.5 M). EDCI (452.5 mg, 2.36 mmol) was added and the pH was readjusted to 5.6-5.8 with HCl (0.5 M). Polyamine-biotin (5) (114 mg, 0.25 mmol) in water (2 mL) was added and the pH was readjusted to 5.6-5.8 with HCl (0.5 M). The solution was stirred for 3 hours with control of pH at 5.6-5.8. The solution was brought to a pH of 8.5 using triethylamine and the product was separated by anion exchange column (A-25 sephadex) with 0.1-1 M triethyl ammonium carbonate buffer (pH 8.5) as eluent.

Fractions containing APB were combined, lyophilized to dryness, and stored at −80° C. as a white solid (18.9 mg, 36%). Purity (95%) was assessed by RP-HPLC with triethyl ammonium acetate buffer (TEAAB, buffer A: 100 mM TEAAB in HPLC water) and acetonitrile (buffer B: 100% acetonitrile) using constant 5% buffer B for 10 minutes and then a gradient of 5% to 40% buffer B over 40 minutes. $^1$H NMR (400 MHz, D$_2$O): δ 0.92 (4H, t), 1.24 (6H, t), 1.50-1.53 (3H, m), 1.66 (3H, m), 2.05 (1H, t), 2.45 (2H, t), 2.58 (3H, s), 2.71-2.90 (m, 9H), 3.15-3.21 (6H, q), 4.00 (2H, d), 4.18-4.21 (2H, m), 4.35-4.39 (2H, m), 5.91 (2H, d), 8.07 (1H, s), 8.37 (1H, s). $^{13}$C NMR (100 MHz, D$_2$O): δ 25.1 (2), 25.9, 27.6, 27.9, 35.4 (2), 42.2, 44.7, 45.3, 45.4, 47.2 (2), 47.9 (2), 48.6 (2), 53.7 (2), 55.3, 60.1 (2), 61.9, 67.4, 86.5, 118.3, 123.7, 127.7, 139.9, 152.9, 167.6. $^{31}$P NMR (162 MHz, D$_2$O): −1.8 (d), −11.8 (d), −23.1 (t). UV/Vis spectroscopy (H$_2$O): λ 260 nm. HRMS: [M−1]$^-$ for C$_{32}$H$_{58}$N$_{11}$O$_{14}$P$_3$S: calc. 944.3098. found 944.3046.

5. Synthesis of N-Acetylated Kemptide (AcLRRASLG)

Acetyl kemptide was synthesized by Fmoc based solid phase peptide solid according to literature.[4] The peptide was purified by RP-HPLC and characterized by MALDI-TOF, [M+1]$^+$ for C$_{34}$H$_{63}$N$_{13}$O$_{10}$$^+$: Calc. 814.4894. found 814.372.

6. In Vitro Kinase-Catalyzed Biotinylation of MBP with PKA

Kinase-catalyzed biotinylation was performed by incubating ATP or APB analog (5 mM), PKA enzyme (5 μg/mL, 500 U), and myelin basic protein (MBP) (1 μg/μL) in the kinase buffer provided by the manufacturer (1×). The final volume for the reaction was 20 μL. The reaction mixture was incubated at 31° C. for 2 hours. Reactions without PKA and/or APB were conducted as control experiments. Reactions in presence of the kinase inhibitor staursporine (1 μM final concentration) were also performed where inhibitor and PKA were preincubated for 30 minutes before addition of APB (FIG. 15). Another control experiment was performed by adding TFA (50% final conc.), and incubating at 45° C. for 1 hr with shaking at 700 rpm to cleave the phosphoramidate bond. TFA was evaporated using speed vac, followed by neutralization of the remaining TFA with 1.5 M Tris base (pH=8.8, 10 μL). All reaction mixtures were separated by 16% SDS-PAGE and visualized with SYPRO® Ruby or transferred onto a polyvinylidene difluoride membrane (Immobilon-P, Milipore) and visualized with streptavidin-Cy5 (Life Technologies).

7. In Vitro MS Analysis of Kinase-Catalyzed Biotinylation

APB analog (5 mM) was incubated with PKA enzyme (20 μg/mL, 2000 U) and N-acetylated kemptide (1 mM) in the kinase buffer provided by the manufacturer (1×). The final volume for the reaction was 10 μL. The reaction mixture was incubated at 31° C. for 2 hours. A reaction without PKA was conducted as a control experiment. The reactions were subsequently mixed with an equal volume (10 μL) of a saturated solution of a 1:1 mixture of 3-hydroxyalpha picolinic acid and alpha-cyano-4-hydroxycinnamic acid in 50% acetonitrile, then spotted on a MALDI plate. The spot was left to dry and analyzed by MALDI-TOF (Bruker). Phosphorylbiotinylated peptide masses were detected at high laser power.

8. In Vitro Quantification of Kinase-Catalyzed Biotinylation of MBP with PKA Kinase-catalyzed phosphorylation and biotinylation reactions were performed as in section V, followed by incubation with TFA (50% final conc.) for 1 hour at 45° C. with shaking at 700 rpm. The TFA incubation was necessary to cleave the phosphoramidate bond in the ATP-biotin products to create a phosphoprotein for quantitative analysis. TFA was evaporated using speed vac, followed by neutralization of the remaining TFA, as described in section V. The reaction mixtures were separated by SDS-PAGE (16%) gel electrophoresis and visualized by SYPRO® Ruby or Pro-Q diamond stain according to the manufacturer's instructions. Quantification of MBP phosphorylation on the Pro-Q diamond stained gel image was performed with ImageQuant 5.2 by drawing the same-sized rectangle on each MBP protein band. The MBP phosphorylation signal was background corrected by subtracting the signal after kinase reaction by the signal of untreated MBP. Percentage phosphorylation was calculated by dividing the background-corrected MBP phosphorylation signal in ATP-biotin or APB reactions by the signal in ATP reactions (set as 100% phosphorylation) and multiplying by 100.

9. Kinetic Analysis of APB with PKA

An NADH-dependent coupled assay was used to perform kinetic analysis, as previously described,[7] with some exceptions. The assay was performed using 0.5 mM NADH, 24 units/mL of pyruvate kinase, 36 units/mL of lactic acid dehydrogenase, PKA (2.5 μg/mL, 61 nM), ATP or ATP-biotin final concentrations of 0.5, 1, 3, 10, 30, and 100 μM, and absorbance at 360 nm taken every 30 second for 60 min. Kaleidagraph software (Synergy Software) and by non-linear regression analysis was used to obtain K$_M$ and V$_{max}$ values from the Michaelis-Mentor equation (v=V$_{max}$*[S]/(K$_M$+[S]), where v=rate of the reaction and [S]=substrate concentration). k$_{cat}$ was calculated by dividing V$_{max}$ by the concentration of PKA enzyme.

10. Hela Cells Lysis Procedure

Hela cells (National Cell Culture Center, Biovest) (20×10$^6$) were lysed in lysis buffer (50 mM Tris, pH 8.0, 150 mM NaCl, 0.5% Triton X-100, 10% glycerol, and 1× protease inhibitor cocktail (GenDepot); 1 mL) with rotation for an hour at 4° C. Cell debris was removed by centrifugation at 13,200 rpm for 10 minutes at 4° C. The supernatant was collected and protein concentration was determined by Bradford assay. Protein content was brought to a working concentration (10 mg/mL) using lysis buffer before storage at −80° C.

11. Kinase-Catalyzed Biotinylation of Hela Cell Lysates

APB (5 mM) or ATP-biotin (5 mM) was incubated with HeLa cell lysates (4 μg/μL) at 30° C. for 2 hours. The final volume of the reaction was 20 μL. Heat-inactivated Hela cell lysates were produced by heating at 95° C. for 5 min before adding APB. NHS-biotin (0.5 mM) was incubated with cell lysates as a positive biotinylation control reaction. As a control to cleave the phosphoramidate bond, TFA (50% final conc.) was added after reaction and incubated for 1 hour at 31° C. with shaking at 800 rpm, followed by evaporation using speed vac, and neutralization by adding 1.5 M Tris base (pH=8.8, 10 μL). The reaction mixtures were separated by SDS-PAGE (10%) and visualized by SYPRO® Ruby or transferred onto a polyvinylidene difluoride membrane (Immobilon-P, Milipore) and visualized with streptavidin-Cy5 (Life Technologies).

12. Kinase-Catalyzed Biotinylation of Hela Cells

Hela cells (200,000 cells) were added to 12-well plates and allowed to grow for 48 h in F-12 media containing 10% FBS, penicillin (9 units), and streptomycin (9 units) at 37° C. in a 5% $CO_2$ environment. The cells were then incubated with ATP-biotin (5 mM) or APB (5 mM) dissolved in F-12 growth media (400 mL) for 1 hr under the same growth conditions as above. As a control, one well was preincubated with staurosporine (1 μM final concentration) in growth media for 1 hour before adding media containing APB. The media was removed and cells were washed with DPBS (400 μL) two times, scraped, and collected by centrifugation at 1000 rpm for 5 min at 0° C. Cell pellets were lysed in lysis buffer (31 μL) on ice for 30 minutes and then lysates were collected as in section VII. The lysate mixtures were separated by 10% SDS-PAGE and visualized by SYPRO® Ruby or transferred onto a polyvinylidene difluoride membrane (Immobilon-P, Milipore) and visualized with streptavidin-Cy5 (Life Technologies).

13. Cell Viability Assay

Hela cells (100,000) were incubated in a 24 well plate and allowed to grow for 48 h in F-12 media containing 10% FBS, penicillin (9 units), and streptomycin (9 units) at 37° C. in a 5% $CO_2$ environment. APB (1, 5, 10, 15, 20, 30 mM) in media (200 uL) was added to cells and cells were incubated for an hour. The media was removed and cells were washed twice with DPBS (400 uL), followed by trypsinization. Cells were collected by centrifugation at 4° C. at 1000 rpm for 5 minutes, followed by washing twice with DPBS (100 uL). Cells were resuspended and an equal volume of cell suspension was mixed with trypan blue (0.4%) and counted using hemocytometer. As a control, untreated cells were counted in one well after subjecting them to the same washing conditions. Percentage viability was calculated by dividing the number of treated live cells by untreated ones. Kaleidagraph software (Synergy Software) was used to calculate $EC_{50}$ of APB. The results are from three independent trials.

14. Fluorescence Microscopy Assay

Hela cells (80,000) were grown on a cover slip in a 24 well plate overnight in F-12 media (500 μL) containing 10% FBS, penicillin (9 units), and streptomycin (9 units) at 37° C. in a 5% $CO_2$ environment until 80% confluency. The cells were then incubated in serum free media for 2 hours, followed by incubation with APB (5 mM) in serum free media (500 μL) for 1 hour. Cells were washed with DPBS (500 μL) 3 times, followed by 1×PBS (500 μL, 137 mM NaCl, 27 KCl, 10 mM $Na_2HPO_4$, 2 mM $KH_2PO_4$) three times. Cells were incubate with paraformaldehyde (4%, 500 μL) for 20 minutes at room temperature, then washed with 1×PBS (500 μL) three times. Triton-X100 (0.2% in PBS) was added and incubated with cells for 5 minutes at room temperature, followed by washing with PBS (500 μL) 3 times each for 5 min. Blocking buffer (2% BSA, 2% normal goat serum, and 0.2% gelatin in 1×PBS) was incubated with cells for 1 hour at room temperature. Streptavidin Cy5 (10 ug/mL) in blocking buffer (50 μL) was added and incubated with cells for 30 minutes. Cells were washed with 0.1% BSA in 1×PBS (500 μL) 3 times each for 5 minutes. Cells were incubated with DAPI (100 μg/mL) for 5 minutes, followed by washing with 1×PBS (500 μL) 3 times each for 5 min. The cover slips were washed in water then installed on a glass slide containing Mowiol mounting solution (50 μL, Sigma Aldrich) saturated with DABCO (Sigma Aldrich). The slide was incubate at 31° C. for 30 minutes, and then kept at 4° C. until microscopy. Fluorescence photos were generated on an Olympus fluorescence microscope using laser wavelengths corresponding to DAPI (350 nm) and Cy5 (650 nm). DAPI photos were generated at 10 ms and Cy5 at 200 ms. Merged images were created using Adobe Photoshop.

Figure 21A:
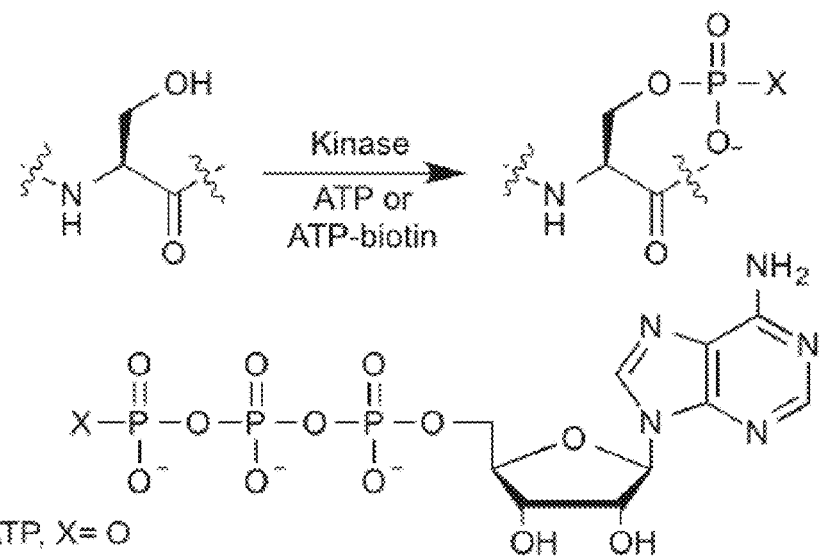
FIGS. 21A, 21B, and 21C. A) Kinase-catalyzed phosphorylation of proteins using ATP or ATP analogs, ATP-biotin or ATP-polyamine-biotin (APB). B) The structures of ATP (X=O), ATP-biotin, or APB. C) The structure of deacetylated chitosan (DC).
Figure 21B:
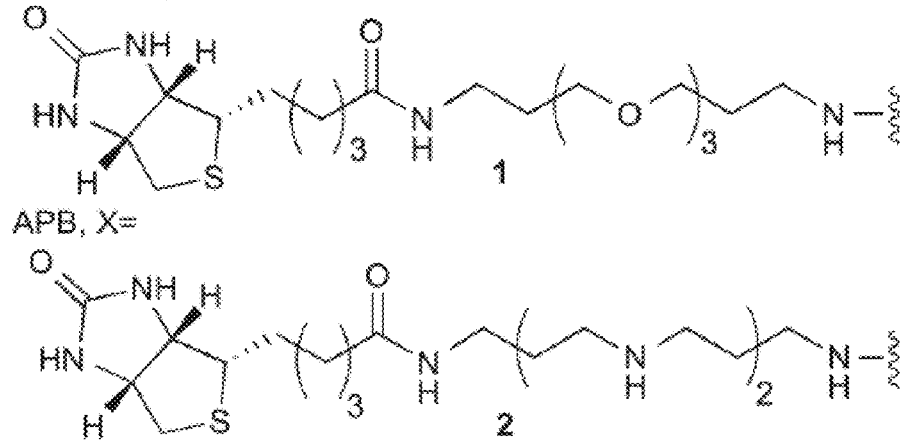

Recently, the first intrinsically cell permeable ATP analog, ATP-polyamine-biotin (APB, FIG. 21b), which is compatible with live cell kinase-catalyzed labeling is set forth above in embodiments of the present invention. The cell permeability of APB is due to the presence of a polyamine linker, which is positively charged under physiological conditions and partially neutralizes the negative charges of the triphosphate. Several additives have also been used to permeabilize ATP and other small molecules. Of these methods, the mild non-ionic detergent digitonin has been used by several research groups to permeabilize ATP analogs. (Paul Holden and William A Horton, BMC Research Notes 2 (2), 243 (2009)). Digitonin interacts specifically with cholesterol and β-hyroxy glycerol on membranes to facilitate permeabilization. Unfortunately, most digitonin-assisted permeabilization studies have been performed with cells in buffer instead of live growing cells in media. The physiological relevance of studies using digitonin permeabilized cells might be compromised due to these "pseudo in cellulo" conditions. In addition, exogenously added ATP partially reversed permeabilization by digitonin, which might lead to low efficiency. Alternative additives that maintain normal growth conditions and high permeabilization efficiency would have immediate use to analyze kinase-mediated signaling pathways with ATP analogs in live cells.

Figure 21C:
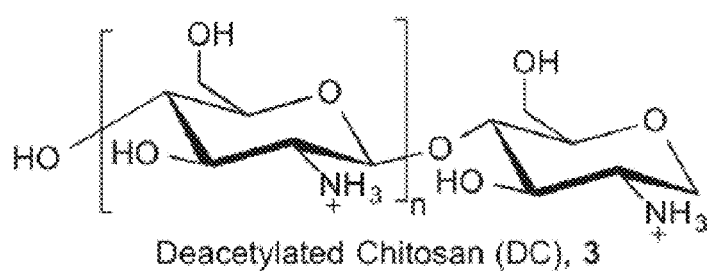

Deacetylated chitosan (DC, FIG. 21c) was reported to chelate ATP and nucleotide-containing drugs to form cell permeable nanoparticles. The cell permeability depended on the ratio of positively charged nitrogens in DC to negatively charged phosphates in ATP (N:P ratio), with the best ratio being 1:1. In addition, DC was used under normal cell growth conditions in media, allowing experiments to be performed using physiologically relevant conditions. Experiments set forth below provide the first application of DC as a vehicle to deliver ATP analogs into cells for in cellulo kinase-catalyzed labeling. The permeabilization and labeling efficiency of DC to digitonin are compared and found higher efficiency with DC. DC permeabilization offers a powerful alternative to use of physiologically-compromised digitonin permeabilization or tedious synthesis of intrinsically permeable ATP analogs.

To test if DC can promote the cell permeabilization of ATP-biotin, fluorescence microscopy studies were performed. ATP-biotin and DC were first preincubated to form a ATP-biotin/DC complex. A 1:1 ratio of ATP-biotin:DC was used based on prior reports studying DC-assisted cell permeability of ATP. The ATP-biotin/DC complex was then incubated with HeLa cells under normal growth conditions, followed by washing, fixing, and staining with streptavidin-Cy5 to detect biotin. As a control, cells were treated with ATP-biotin alone. Only cells treated with the ATP-biotin/DC complex showed significant fluorescence signal (FIG. 22a).

ATP-biotin alone in media showed only background fluorescence. As a comparative control, cells were also incubated with an ATP-biotin/digitonin complex. With the same concentration of ATP-biotin (2 mM) used as in the DC-assisted permeabilization studies, ATP-biotin/digitonin showed only background fluorescence (FIG. 2b). These experiments indicated that DC promotes the cell permeability of ATP-biotin under normal cell growth conditions with high efficiency.

As a secondary method to confirm ATP-biotin cell delivery by DC, mass spectrometry (MS) analysis was used. HeLa cells were incubated with ATP-biotin or the ATP-biotin/DC complex, washed, and analyzed by MALDI-TOF (Mass assisted laser desorption ionization-time of flight) MS. Only cells treated with the ATP-biotin/DC complex showed a peak at 934 m/z corresponding to ATP-biotin (FIG. 22c). Cells treated with ATP-biotin alone did not show the presence of m/z 934 peak. These results confirm that DC promotes the cell permeability of ATP-biotin.

In preparation for cell labeling, the dose dependent cytotoxicity of ATP-biotin/DC in HeLa cells was accessed. The ATP-biotin/DC complex showed an $EC_{50}$ of 8.0±0.6 mM/7.5±0.6 mg/mL, respectively (Fig. S1). HeLa cells showed viability of 79±5% for ATP-biotin/DC concentrations used in later kinase-catalyzed biotinylation reactions (4 mM/3.75 mg/mL). For comparison, the cytotoxicity of ATP-biotin/digitonin was also tested and observed only 55±3% cell viability at the concentrations used in later biotinylation reactions (4 mM/20 μg/mL, Fig. S1). Taken together, these studies indicated that DC is less cytotoxic than digitonin at concentrations needed for cell permeability.

Having confirmed the cell permeability and low toxicity of DC, kinase-catalyzed biotinylation in live cells were tested. HeLa cells growing in culture were incubated with ATP-biotin/DC complex, followed by washing, harvesting, lysis, and separation of proteins by SDS-PAGE. Biotinylation was observed in cells treated with the ATP-biotin/DC complex (FIG. 23a, lane 5), which is consistent with its cell permeability. As a control, HeLa cells pretreated with the kinase inhibitor, staurosporine, showed reduced biotinylation (FIG. 23a, lane 4), which confirms that biotinylation is kinase dependent. ATP-biotin alone did not show labeling (FIG. 23a, lane 2), which indicates that DC is required for cell permeability. These experiments establish that DC-permeabilization is compatible with live cell labeling.

As a comparative control, we tested the ability of digitonin to promote in cellulo kinase-catalyzed labeling. Using similar conditions to the DC permeabilization studies, cells were incubated with a ATP-biotin/digitonin mixture under normal growth conditions and then analyzed by gel methods. No biotinylation was observed (FIG. 23c, lane 13), indicating a low efficiency of permeabilization. Similar results were also observed when cells were incubated with a ATP-biotin/digitonin mixture in buffer (FIG. 23c, lane 14). As a further comparison, harvested cells were digitonin-permeabilized in buffer using the condition published previously.[20] In this case, cells were harvested, washed, permeabilized with digitonin in buffer, and then incubated with ATP-biotin in buffer. With harvested cells, biotinylation of cellular proteins was observed (FIG. 30, lanes 4 and 8), although at lower levels compared to DC-assisted biotinylation (FIG. 23a, lane 5). These results document that DC permeabilization offered greater labeling efficiency under normal cell growth conditions compared to digitonin permeabilization.

Most experiments with ATP analogs have been performed in lysates, not live cells. Therefore, live cell biotinylation versus lysate labeling was evaluated. To compare in cellulo to in vitro labeling, ATP-biotin was incubated with HeLa cell lysates and the biotinylated proteins were analyzed by gel methods (FIG. 23b). The extent of in cellulo DC-assisted biotinylation (FIG. 23a, lane 5) compared to in vitro labeling (FIG. 23b, lane 8) was different. In particular, lysate biotinylation produced different labeled bands compared to in cellulo labeling. The differences observed with DC-assisted in cellulo biotinylation compared to lysate labeling are consistent with earlier studies using an intrinsically cell permeable ATP-biotin analog. (A. E. Fouda and M. K. Pflum, *Angew Chem Int Ed Engl* 54 (33), 9618 (2015); the entire disclosure of which is hereby incorporated by reference). The difference in biotinylation in live cells versus lysates may be due to cellular compartmentalization, which suggests that in cellulo ATP-biotin labeling will better reflect the cellular phosphoproteome than lysate-based labeling.

In conclusion, this study documents use of DC to permeabilize ATP analogs for cell-based studies. Compared to other methods, DC-assisted permeabilization offers several advantages. DC can be generally applied to permeabilize any ATP analog, which avoids synthesis of intrinsically cell permeable ATP derivatives. Importantly, DC permeabilization is compatible with normal cell growth conditions for more physiologically relevant studies. In fact, a comparison of live cell versus lysate labeling documented differences in the quality of biotinylation, suggesting that in cellulo studies will be valuable. DC permeabilization represents an exciting advance to the study cell signaling using ATP analogs under physiologically relevant conditions Materials Low molecular weight deacetylated chitosan (75-85% deacetylation), digitonin, 1,4-Diazabicyclo[2.2.2]octane (DABCO), and Mowiol® 4-88 were purchased from Sigma Aldrich. ATP was bought from MP Biomedicals. 1-(3-Dimethylaminopropyl)-3-ethylcarbodiimide hydrochloride (EDCI) and N,N,N',N'-Tetramethylethylenediamine for electrophoresis were purchased from Acros. F12 media, silica, DEAE sephadex A-25, and Ammonium persulfate (APS) for electrophoresis were bought from Fisher Scientific. Dichloromethane (DCM), acetic acid, and hydrochloric acid were bought from EMD. 40% Bis-acrylamide (37.5:1) for gel electrophoresis was purchases from Biorad. Fetal bovine serum (FBS) was bought from Gibco-Invitrogen. Antibiotic and Dulbecco's Phosphate Buffered Saline (DPBS) for cell culture were purchased from HyClone. DAPI was purchased from Life-Technology.

Instruments

SDS-PAGE apparatus was purchased from BioRad (Protean III). Mini-Transblot Electrophoretic Transfer Cell apparatus from BioRad was used in Protein transfer. A Typhoon 9210 scanner (Amersham Biosciences) was used to visualize SDS gels and PVDF membranes. An Olympus immunofluorescence microscope (Model BX 41) was used to visualize fluorescence images. ATP-biotin was detected using an MTP Plate (Bruker) and MALDI-TOF mass spectrometer (Bruker ultraflex).

Experimental Procedures

1. Synthesis of ATP-Biotin

ATP-biotin was synthesized as previously reported. (Senevirathne, C.; Pflum, M. K. H., Biotinylated Phosphoproteins from Kinase-Catalyzed Biotinylation are Stable to Phosphatases: Implications for Phosphoproteomics. *Chem Bio Chem* 2013, 381-387; the entire disclosure of which is hereby incorporated by reference).

2. Preparation of Deacetylated Chitosan

Deacetylated chitosan (DC, 75%-85% deacetylated, 500 mg) was triturated with 1.75% acetic acid in water (50 mL). The mixture was stirred overnight at room temperature to produce a homogenous solution.

3. Preparation of ATP-Biotin/DC Mixture

ATP-biotin (32 mM, 50 µL) was added portion wise to the deacetylated chitosan solution (10 mg/mL, 150 µL) with vortexing. The mixture was diluted with either water (4 µL) or staurosporine (4 µL, 1 µM final concentration) and the volume was adjusted to 400 µL using growth media containing F-12 media, 10% fetal bovine serum (FBS), penicillin (9 units), and streptomycin (9 units). The solution used for kinase-catalyzed biotinylation contained an ATP-biotin at a final concentration of 4 mM and DC at a final concentration of 3.75 mg/mL. To create mixtures used in the cell viability studies, the concentration of the initial solutions were adjusted to ultimately lead to the desired concentrations.

4. Cell Viability Assessment of DC

Figure 24A:
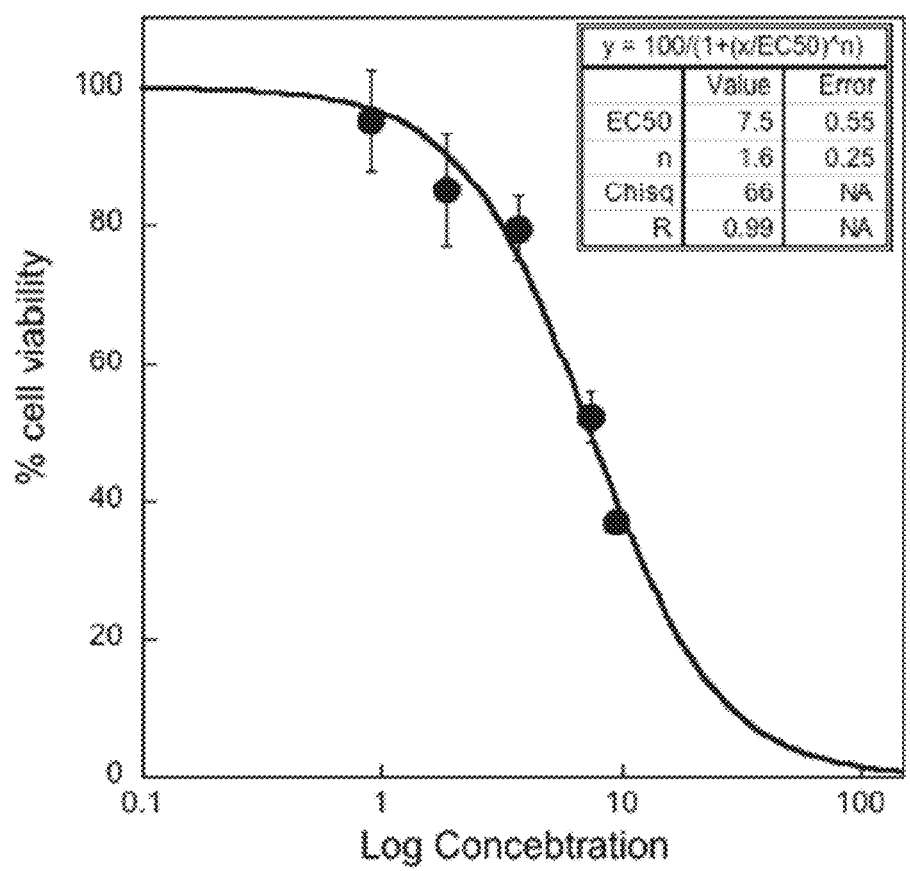
Figure 25A:
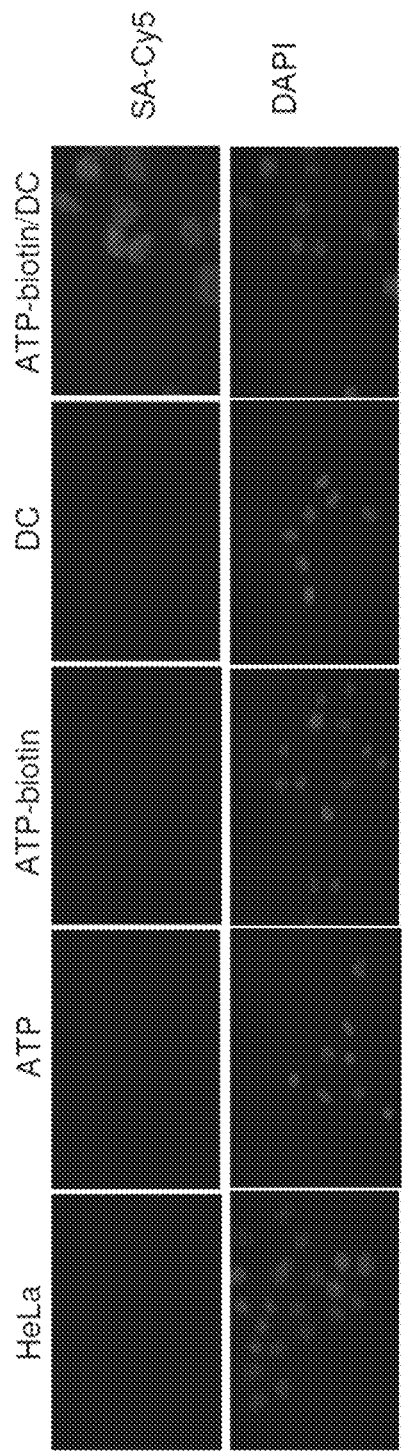
FIGS. 25A and 25B. Repetitive trials of fluorescence microscopy experiments visualizing ATP-biotin in HeLa cells after incubation with the ATP-biotin/DC complex. HeLa cells were incubated with ATP, ATP-biotin, DC, or the ATP-biotin/DC complex, followed by washing, fixing, permeabilizing, and visualization with Streptavidin-Cy5 (SA-Cy5, top) or DAPI (bottom).
Figure 25B:
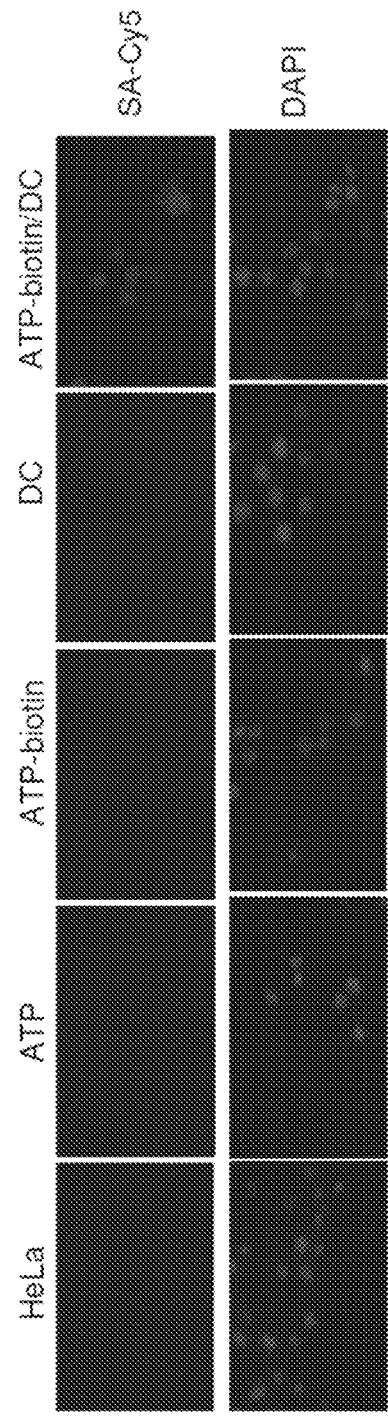
Figure 26A:
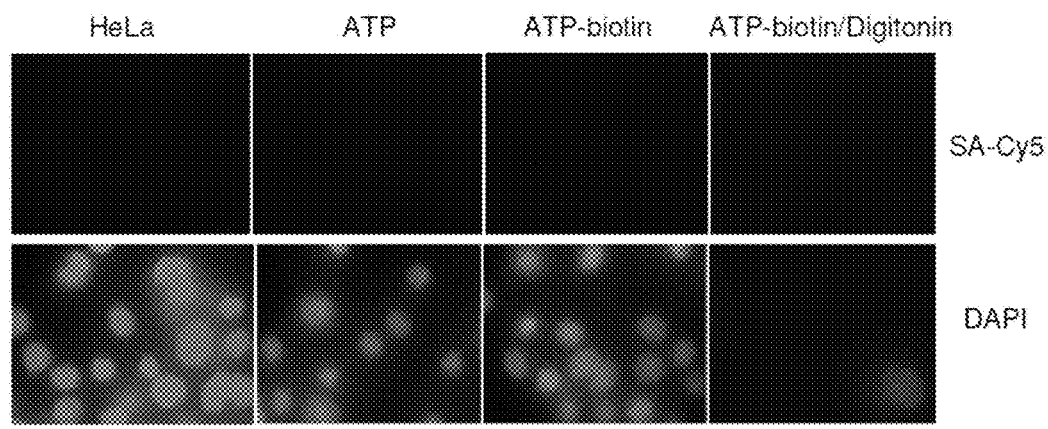
FIGS. 26A and 26B. Repetitive trials of fluorescence microscopy experiments visualizing ATP-biotin in HeLa cells after incubation with the ATP-biotin/digitonin complex. HeLa cells were incubated with ATP, ATP-biotin, digitonin, or the ATP-biotin/digitonin complex, followed by washing, fixing, permeabilizing, and Cells visualization with Streptavidin-Cy5 (SA-Cy5, top) and DAPI (bottom).
Figure 26B:
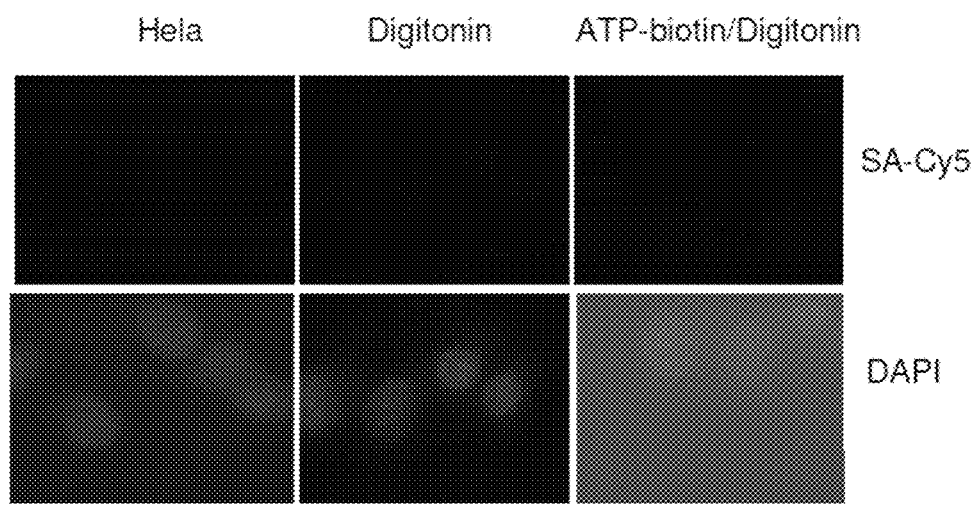

HeLa cells (100,000 cells) were grown in a 12 well plate for 48 hours in F-12 media containing 10% FBS, penicillin (9 units), and streptomycin (9 units) at 37° C. in a 5% $CO_2$ environment. Various concentrations of the ATP-biotin/DC complex (1 mM/0.9 mg/mL, 2 mM/1.88 mg/mL, 4 mM/3.75 mg/mL, 8 mM/7.5 mg/mL, or 10 mM/9.4 mg/mL) were prepared in media as described in section III.3. Each ATP-biotin/DC mixture was added separately to cells. Cells were incubated for 2 hours at 37° C. in a 5% $CO_2$ environment and then the complex was removed. Cells were washed twice with DPBS (400 µL, 8 mM $Na_2HPO_4$, 1.5 mM $KH_2PO_4$, pH 7.4, 137.9 mM NaCl, 2.6 mM KCl), followed by gentle scraping. Cells were collected by centrifugation at 4° C. and 1000 rpm for 5 minutes, followed by resuspension in DPBS (100 µL). Equal volumes of cell suspension and trypan blue (0.4%) were mixed and cells were counted using a hemocytometer. As a control, untreated cells grown in the absence of ATP-biotin/DC were counted, as described. Percentage cell viability was calculated by dividing the number of ATP-biotin/DC-treated live cells by untreated ones, and multiplied by 100. Kaleidagraph software (Synergy Software) was used to calculate the $EC_{50}$ of ATP-biotin/DC using a sigmoidal binding curve ($y=100/(1+(x/EC_{50})^n)$). The results shown are from three independent trials (FIG. 24).

5. Cell Viability Assessment of Digitonin

Cells were prepared and treated as described in section 4, except the following. Cells were treated with ATP-biotin (4 mM) and digitonin (20 µg/mL) in P buffer (400 µL; 25 mM Tris-HCl, pH 7.5, 7.2 mM $Na_2HPO4$, 1.4 mM $KH_2PO_4$, pH 7.4, 124 mM NaCl, 2.3 mM KCl, 2 mM dithiothreitol (DTT), and 10 mM $MgCl_2$) containing Xpert protease inhibitor cocktail (1×, GenDEPOT) for 1 hour at 37° C. in a 5% $CO_2$ environment. As a control, cells were also treated with ATP-biotin (4 mM) and digitonin (20 µg/mL) in growth media (F-12 media, 10% FBS, penicillin (9 units), and streptomycin (9 units)) for 1 hour at 37° C. in a 5% $CO_2$ environment. Digitonin treatment was restricted to one hour due to high toxicity at longer times.

6. Fluorescence Microscopy Assay

HeLa cells (160,000 cells) were grown on a glass cover slip in a 12 well plate overnight in F-12 media (500 µL) containing 10% FBS, penicillin (9 units), and streptomycin (9 units) at 37° C. in a 5% $CO_2$ environment. Cells were then incubated in serum-free F12 media for 1 hour at 37° C. in a 5% $CO_2$ environment. After the media was removed, cells were incubated for 2 hours at 37° C. in a 5% $CO_2$ environment with serum free media (in case of DC) or P buffer (in case of digitonin) (400 µL) containing one of the following: ATP (2 mM), ATP-biotin alone (2 mM), DC alone (1.9 mg/mL), digitonin alone (20 µg/mL), ATP-biotin/DC (2 mM/1.9 mg/mL), or ATP-biotin/digitonin (2 mM/20 µg/mL). Cells were washed with DPBS (500 µL) three times, followed by washing with PBS (500 µL) three times. Paraformaldehyde (4% in water, 500 µL) was added and incubated for 20 minutes at room temperature to fix cells, followed by washing three times with PBS (500 µL, 2 mM $KH_2PO_4$, 10 mM $Na_2HPO_4$, pH 7.4, 137 mM NaCl, 2.7 mM KCl). Cells were incubated with Triton X-100 (0.2% in PBS, 500 µL) for 5 minutes at room temperature, followed by washing with PBS (500 µL) three times each for 5 min. Cells were incubated with blocking buffer (2% BSA, 2% normal goat serum, and 0.2% gelatin) for 1 hour at room temperature, followed by incubation of cells with Streptavidin-Cy5 (10 µg/mL) in blocking buffer (50 µL) for 30 minutes. Cells were washed with BSA (0.1% in PBS, 500 µL) three times, each for 5 minutes. DAPI (100 µg/mL in blocking buffer) was added to cells for 5 minutes, followed by washing with PBS (500 µL) three times each for 5 min. Cover slips were immersed in water then fixed on a glass slide containing a solution of Mowiol® 4-88 saturated with DABCO (6 µL), as described by the manufacturer (Sigma-Aldrich). The slide was incubated at 31° C. for 30 minutes, then kept at 4° C. until microscopy. An Olympus microscope was used to monitor fluorescence signal using laser wavelengths corresponding to DAPI (excitation/emission maximum 358/461 nm) and Cy5 (excitation/emission maximum 678/694 nm). DAPI images were generated at 10 ms, whereas Cy5 images were generated at 500 ms. Three independent trials are shown in FIGS. 22a, 22b, 25, and 26.

7. MALDI in Cellulo Imaging of ATP-Biotin

Figure 27A:
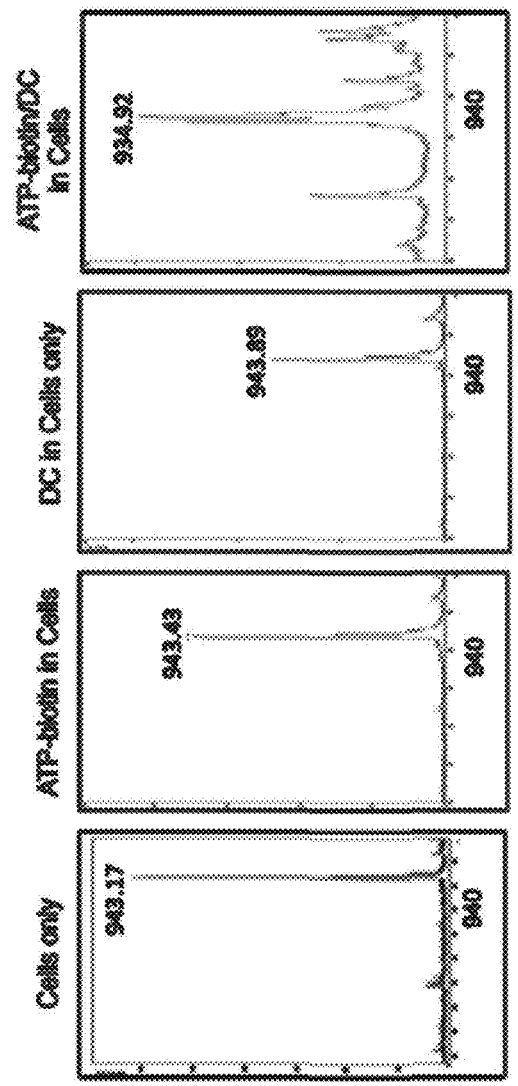
FIGS. 27A and 27B. Repetitive trials of MALDI-TOF MS monitoring of ATP-biotin in HeLa cells after incubation with the ATP-biotin/digitonin complex. HeLa cells were incubated with ATP-biotin, DC, or the ATP-biotin/DC complex, followed by washing and mixing with α-picolinic acid in 50% acetonitrile. The mixture was spotted on Bruker MALDI plate and analyzed for the presence of ATP-biotin at 934 m/z. The 943 m/z peak represents a contaminant in the cells.
Figure 27B:
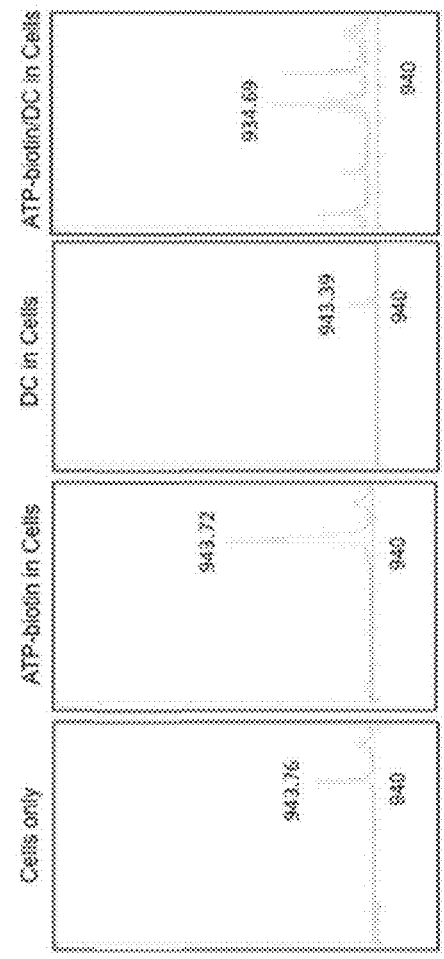
Figures 28A, 28B:
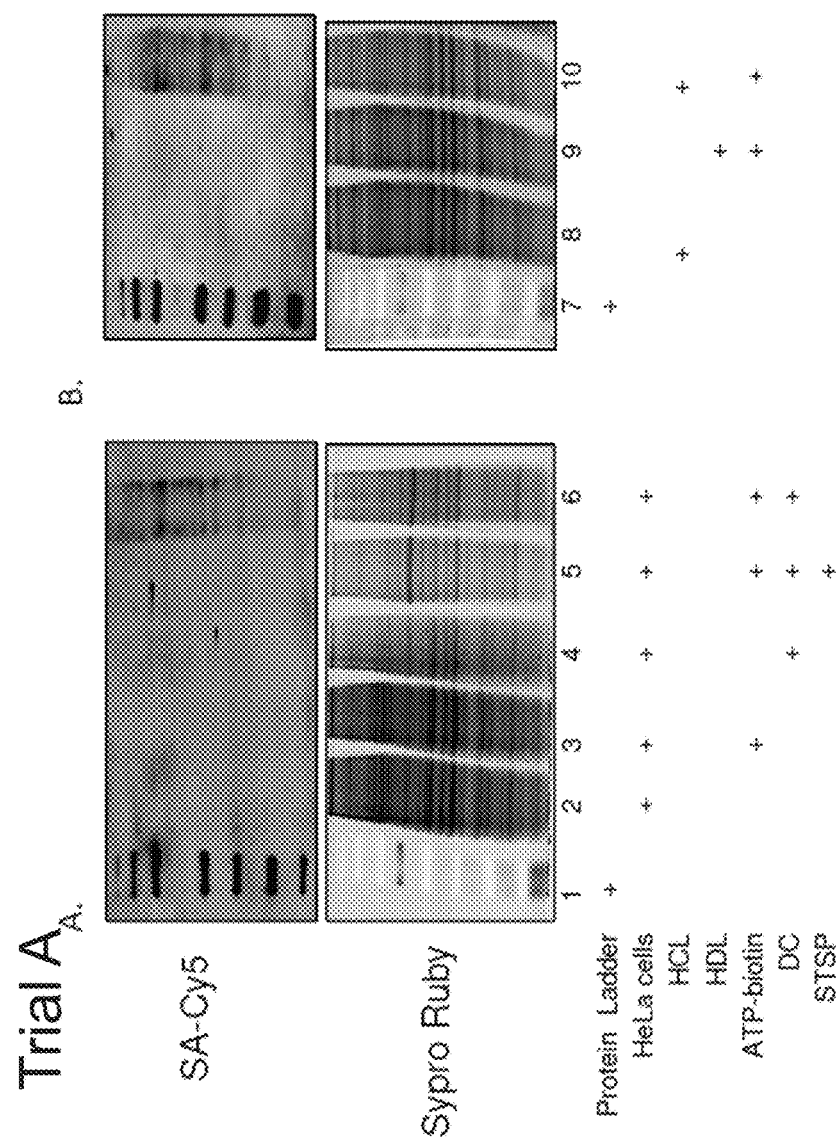

HeLa cells (20,000 cells) were suspended in F-12 media containing 11% FBS, penicillin (9 units) and streptomycin (9 units) (50 mL), then added to a well of a 96 well plate. An equal volume (50 µL) of final concentrations of ATP-biotin (4 mM), DC (3.75 mg/mL), or ATP-biotin/DC complex (4 mM/3.75 mg/mL) was added to separate wells and cells were incubated for 2 hours at 37° C. in a 5% $CO_2$ environment. As a control, one well without ATP analog was used as a reference. All reaction volumes were 100 mL. Cells were collected by centrifugation at 1000 rpm for 5 min at 4° C., then washed twice with DPBS (100 mL). Cell pellets were resuspended in water (20 mL). The cell suspension (1 mL) was mixed with a saturated solution of α-picolinic acid in 50% acetonitrile (1 mL), and then applied to a MALDI plate (Bruker) for MS analysis. The MS spectra were analyzed for the presence of ATP-biotin at m/z 934. Three independent trials are shown in FIGS. 2c and 27.

8. DC-Assisted in Cellulo Kinase-Catalyzed Biotinylation of HeLa Cells

HeLa cells (200,000 cells) were grown in 12-well plates for 48 hours in F-12 media containing 10% FBS, penicillin (9 units), and streptomycin (9 units) at 37° C. in a 5% $CO_2$ environment. The media was removed and then cells were then incubated with ATP-biotin alone (4 mM) or the ATP-biotin/DC complex (4 mM/3.75 mg/mL) in growth media containing 10% FBS, penicillin (9 units), and streptomycin (9 units) for 2 hours under the same cell growth conditions. As a control, cells were preincubated with staurosporine (1

μM) in media containing 10% FBS, penicillin (9 units), and streptomycin (9 units) at 37° C. in a 5% $CO_2$ environment for 1 hour before incubating with the ATP-biotin/DC mixture. After the media was removed, cells were washed with DPBS (400 μL) two times, harvested by scraping, and collected by centrifugation at 1000 rpm for 5 min at 0° C. Cells were lysed by resuspending in lysis buffer (21 μL, 50 mM Tris, pH 8.0, 150 mM NaCl, 0.5% Triton X-100, 10% glycerol, and 1× protease inhibitor cocktail (GenDepot)) and incubating on ice for 30 minutes with rocking. Lysates were collected by removing cell debris through centrifugation at 13,200 rpm for 10 minutes at 4° C. SDS-PAGE gel analysis (10%) was used to separate cell lysates and total protein was visualized by SYPRO® Ruby stain. Biotinylation was detected with a streptavidin-Cy5 conjugate (Life Technologies) after transferring onto a polyvinylidene difluoride membrane (Immobilon-P, Milipore). The gels were images using a Typhoon imager (GE Healthcare Life Sciences) using excitation and emission wavelengths of 650 nm and 670 nm.

9. Digitonin-Assisted in Cellulo Biotinylation in Buffer and Media

Figure 29:
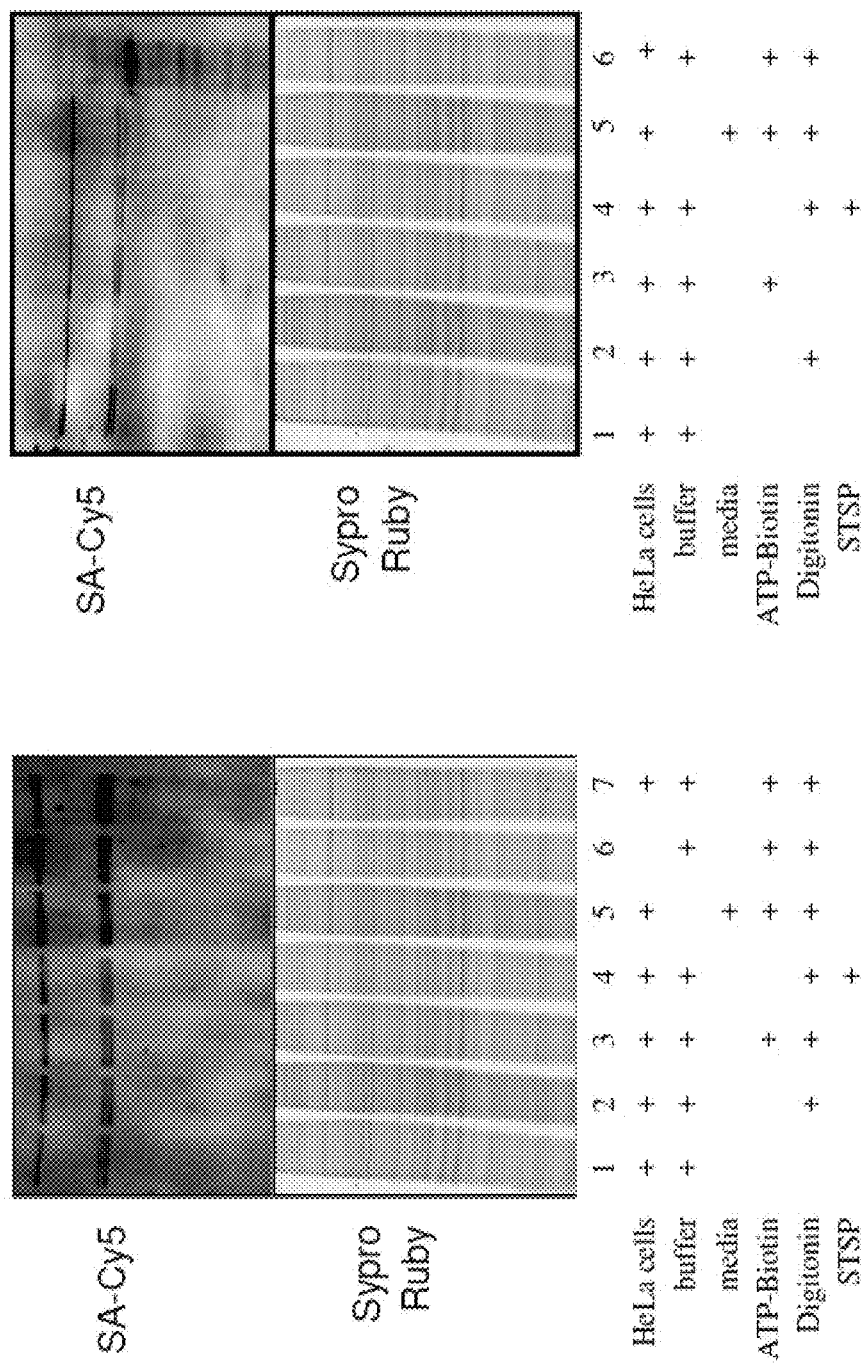
FIGS. 29A and 29B. Repetitive trials of digitonin-assisted in cellulo kinase-catalyzed biotinylation in buffer and normal cell conditions. As a control, HeLa cells were preincubated with kinase inhibitor staurosporine (STSP) to prevent kinase catalysis (lane 4). SDS-PAGE gel analysis was used to separate reaction mixtures and gels were visualized with streptavidin-Cy5 (SA-Cy5, top gels) or SYPRO® Ruby total protein stain (bottom gels). All images are representative of at least three independent trials.

HeLa cells (200,000 cells) were grown in 12-well plates for 48 hours in F-12 media containing 10% FBS, penicillin (9 units), and streptomycin (9 units) at 37° C. in a 5% $CO_2$ environment. Cells were treated with ATP-biotin (4 mM) in the absence or presence of digitonin (20 μg/mL) in P buffer (400 μL) for 1 hour at 37° C. in a 5% $CO_2$ environment. To confirm labeling was kinase dependent, cells were preincubated with staurosporine (1 μM) in P buffer (400 μL) for 30 min at 37° C. in a 5% $CO_2$ environment before removal and subsequent addition of ATP-Biotin and digitonin with staurosporine (1 μM) in P buffer (400 As a comparative control, cells were treated with ATP-biotin (4 mM) and digitonin (20 μg/mL) in F-12 media (400 μL) containing 10% FBS, penicillin (9 units), and streptomycin (9 units) for 2 hours at 37° C. After incubation, the buffer or media was removed, cells were washed with DPBS (400 μL) three times, and cells were harvested by centrifugation at 1000 rpm for 5 min at 0° C. Cell lysates were created and proteins were analyzed by SDS-PAGE as described in section III.8. Repetitive trials are shown in FIGS. 23c and 29.

10. Digitonin-Assisted Pseudo in Cellulo Biotinylation in Buffer

HeLa cells (2×10⁶ cells) were collected, washed with DPBS, and permeabilized for 5 min on ice with 50 μg/mL digitonin in P buffer (400 After permeabilization, the P buffer containing digitonin was removed and cells were washed once with cold DPBS (400 Cell were then treated with ATP-biotin (4 mM) in P buffer (400 μL) for 2 hours at 31° C. with mild shaking at 100 rpm. As a control, cell pellets were incubated with P buffer (400 μL) in the absence of digitonin before the ATP-biotin was added. After incubation, cells were washed with DPBS (400 μL) three times, and cell lysates were created as in section III.8. Proteins were visualized using SDS-PAGE analysis as described in section III.8. Repetitive trials are shown in FIG. 30.

11. Kinase-Catalyzed Biotinylation of Lysates

HeLa cells (200,000 cells) were grown in 12-well plates for 48 hours in F-12 media containing 10% FBS, penicillin (9 units), and streptomycin (9 units) at 37° C. in a 5% $CO_2$ environment. Cells were collected and lysates were prepared as described in section III.8. Lysates were incubated with ATP-biotin (4 mM) for 2 hours at 37° C. in a total reaction volume of 20 μL. As a control, ATP-biotin (4 mM) was incubated with heat denatured cell lysates, which were generated by heating the lysates to 95° C. for 1 min. Proteins were visualized using SDS-PAGE analysis as described in section III.8.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A cell permeable ATP analog having the following formula:

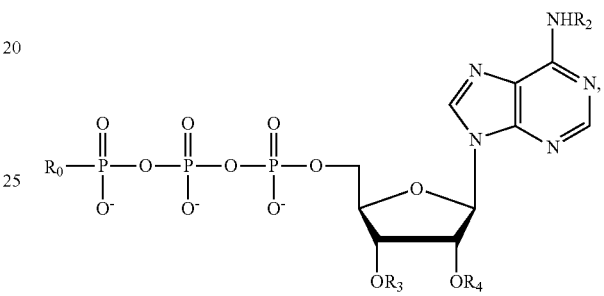

or a physiologically or pharmaceutically acceptable salt thereof, wherein:

$R_0$ is

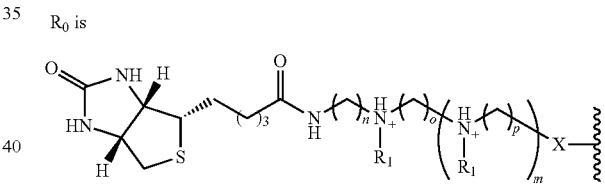

n, o, p are each independently 1, 2, 3, 4, 5, or 6;
m is 0, 1, 2, 3, 4, or 5;
X is O, S, NH, or $CH_2$;
$R_1$ is H or $C_{1-6}$ alkyl,
$R_2$ is H, $C_{1-6}$ alkyl, $C_{6-30}$ aryl, $C_{5-32}$ heteroaryl, or $C_{7-32}$ alkylaryl; and
$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

2. The cell permeable ATP analog of claim 1 wherein $R_1$ is H, methyl, ethyl, isopropyl or propyl and $R_2$, $R_3$, $R_4$ are each independently H.

3. The cell permeable ATP analog of claim 1 wherein $R_1$ is H or methyl and $R_2$, $R_3$, $R_4$ are each independently H.

4. The cell permeable ATP analog of claim 1 wherein is methyl, ethyl, propyl,

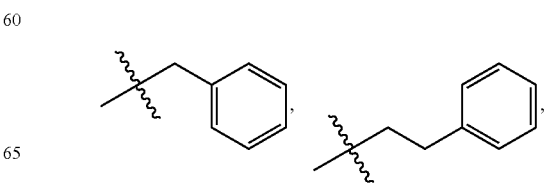

-continued

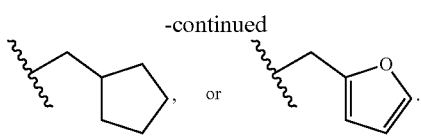

5. The cell permeable ATP analog of claim 1 wherein $R_3$, $R_4$ are each independently H, methyl, ethyl, propyl,

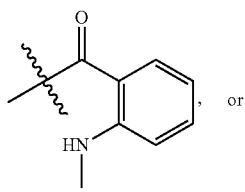

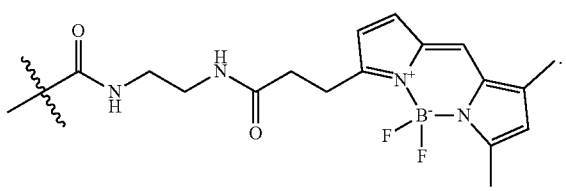

6. The cell permeable ATP analog of claim 1 having the following formula:

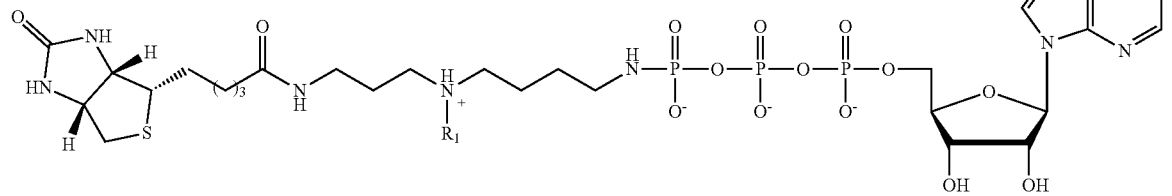

7. The cell permeable ATP analog of claim 1 having the following formula:

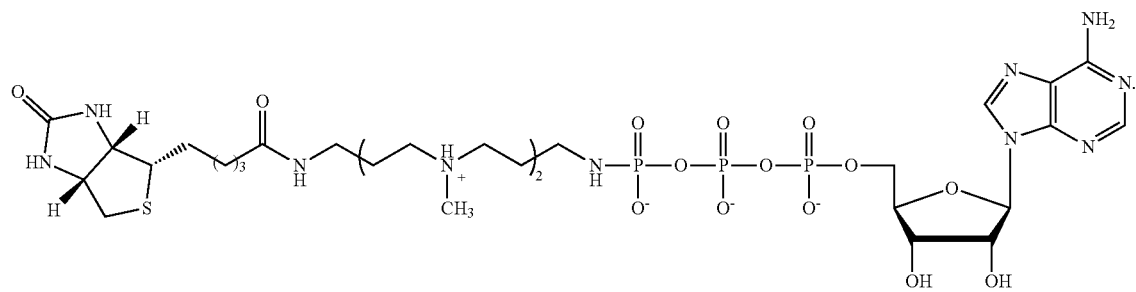

8. The cell permeable ATP analog of claim 1 wherein n is 3, o is 4, p is 3, and m is 1.

9. The cell permeable ATP analog of claim 1 wherein the cell permeable ATP analog and chitosan combine to form a particle.

10. The cell permeable ATP analog of claim 1 wherein the cell permeable ATP analog and deacetylated chitosan combine to form a particle.

11. The cell permeable ATP analog of claim 10 wherein the particle has a size from 100 to 1000 nm.

12. A compound having the following formula:

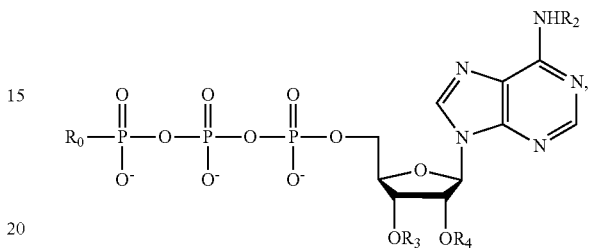

or a physiologically or pharmaceutically acceptable salt thereof, wherein:

$R_0$ is

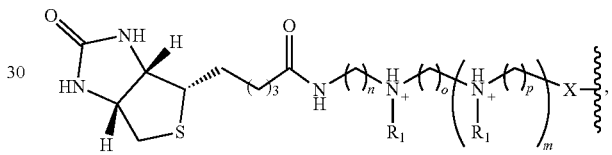

n, o, p are each independently 1, 2, 3, 4, 5, or 6;
m is 0, 1, 2, 3, 4, or 5;

X is O, S, NH, or $CH_2$;

$R_1$ is H or $C_{1-6}$ alkyl, $R_2$ is H, $C_{1-6}$ alkyl, $C_{6-30}$ aryl, $C_{5-32}$ heteroaryl, or $C_{7-32}$ alkylaryl; and $R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

13. A cell permeable ATP analog having the following formula:

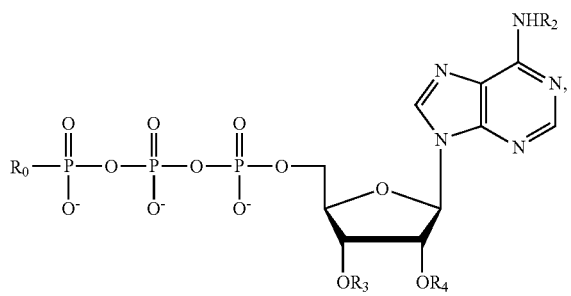

or a physiologically or pharmaceutically acceptable salt thereof, wherein:

$R_0$ is

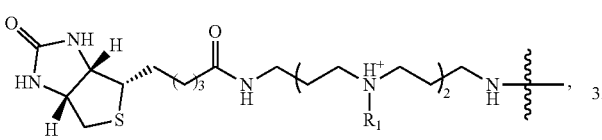

$R_1$ is H or $C_{1-6}$ alkyl, $R_2$ is H, $C_{1-6}$ alkyl, $C_{6-30}$ aryl, $C_{5-32}$ heteroaryl, or $C_{7-32}$ alkylaryl;

$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

14. The cell permeable ATP analog of claim 13 wherein $R_1$ is H, methyl, ethyl, or propyl and $R_2$, $R_3$, $R_4$ are each independently H.

15. The cell permeable ATP analog of claim 13 wherein $R_1$ is H or methyl and $R_2$, $R_3$, $R_4$ are each independently H.

16. The cell permeable ATP analog of claim 13 wherein is methyl, ethyl, or propyl,

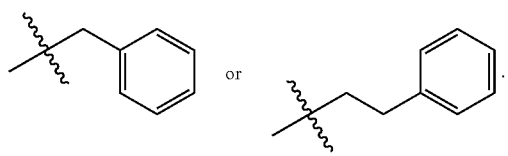

17. The cell permeable ATP analog of claim 13 wherein $R_3$, $R_4$ are each independently H, methyl, ethyl, propyl,

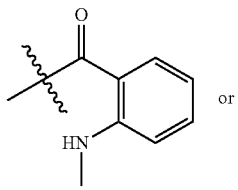

or

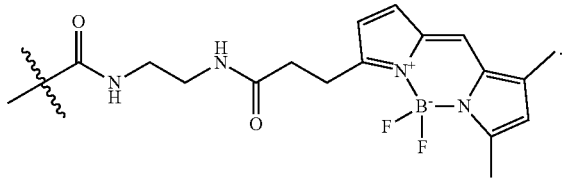

18. The cell permeable ATP analog of claim 13 wherein the cell permeable ATP analog and chitosan combine to form a particle.

19. The cell permeable ATP analog of claim 13 wherein the cell permeable ATP analog and deacelylated chitosan combine to form a particle.

20. A method for introducing cell permeable ATP analog into a cell from a subject, the method comprising:

a) contacting a cell with a cell permeable ATP analog having the following formula:

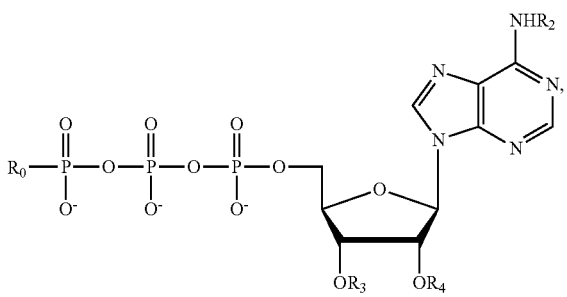

or a physiologically or pharmaceutically acceptable salt thereof, wherein:

$R_0$ is

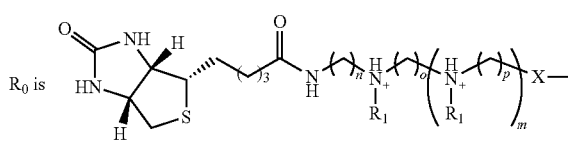

n, o, p are each independently 1, 2, 3, 4, 5, or 6;

m is 0, 1, 2, 3, 4, or 5;

X is O, S, NH, or $CH_2$;

$R_1$ is H or $C_{1-6}$ alkyl, $R_2$ is H, $C_{1-6}$ alkyl, $C_{6-30}$ aryl, $C_{5-32}$ heteroaryl, or $C_{7-32}$ alkylaryl;

$R_3$, $R_4$ are each independently H, $C_{1-6}$ alkyl, $C_{6-30}$ aryl, $C_{5-32}$ heteroaryl, or $C_{7-32}$ alkylaryl, wherein $R_3$, and $R_4$ can be combined together to form a ring structure.

21. The method of claim 20 further comprising:

b) determining if the cell permeable ATP analog has entered the cell with a portion of the cell permeable ATP analog having attached a protein substrate.

22. The method of claim 20 wherein the cell permeable ATP analog further comprises chitosan.

23. The method of claim 20 wherein the cell permeable ATP analog further comprises deacetylated chitosan.

* * * * *